US011697666B2

(12) United States Patent
Johnson et al.

(10) Patent No.: US 11,697,666 B2
(45) Date of Patent: Jul. 11, 2023

(54) METHODS OF PREPARING CARBANUCLEOSIDES USING AMIDES

(71) Applicant: Gilead Sciences, Inc., Foster City, CA (US)

(72) Inventors: Trevor C. Johnson, San Mateo, CA (US); Matthew Kraft, Belmont, CA (US); Marshall D. Young, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/720,704

(22) Filed: Apr. 14, 2022

(65) Prior Publication Data

US 2022/0372057 A1     Nov. 24, 2022

Related U.S. Application Data

(60) Provisional application No. 63/175,724, filed on Apr. 16, 2021.

(51) Int. Cl.
*C07H 9/06*     (2006.01)
*C07H 7/06*     (2006.01)

(52) U.S. Cl.
CPC ................ *C07H 9/06* (2013.01); *C07H 7/06* (2013.01)

(58) Field of Classification Search
None
See application file for complete search history.

(56) References Cited

U.S. PATENT DOCUMENTS

| | | | |
|---|---|---|---|
| 4,707,540 A | 11/1987 | Manser et al. | |
| 5,446,137 A | 8/1995 | Maag et al. | |
| 6,699,994 B1 | 3/2004 | Babu et al. | |
| 8,101,745 B2 | 1/2012 | Hostetler et al. | |
| 8,119,607 B2 | 2/2012 | Francom et al. | |
| 8,242,085 B2 | 8/2012 | Babu et al. | |
| 8,318,700 B2 | 11/2012 | Hostetler et al. | |
| 8,440,813 B2 | 5/2013 | Babu et al. | |
| 9,370,528 B2 | 6/2016 | Schentag et al. | |
| 9,388,208 B2 | 7/2016 | Clarke et al. | |
| 9,701,682 B2 | 7/2017 | Clarke et al. | |
| 9,724,360 B2 | 8/2017 | Chun et al. | |
| 9,777,035 B2 | 10/2017 | Girijavallabhan et al. | |
| 9,815,864 B2 | 11/2017 | Beigelman et al. | |
| 10,004,719 B1 | 6/2018 | Hsu et al. | |
| 10,059,716 B2 | 8/2018 | Clarke et al. | |
| 10,251,904 B2 | 4/2019 | Clarke et al. | |
| 10,377,761 B2 | 8/2019 | Clarke et al. | |
| 10,682,368 B2 | 6/2020 | Perron et al. | |
| 2002/0035082 A1 | 3/2002 | Grinstaff et al. | |
| 2002/0188137 A1 | 12/2002 | Dershem et al. | |
| 2003/0170891 A1 | 9/2003 | McSwiggen | |
| 2003/0175950 A1 | 9/2003 | McSwiggen | |
| 2003/0199516 A1 | 10/2003 | Moser et al. | |
| 2004/0009959 A1 | 1/2004 | Potter et al. | |
| 2004/0157838 A1 | 8/2004 | Griffith | |
| 2004/0157839 A1 | 8/2004 | Griffith | |
| 2004/0214837 A1 | 10/2004 | Griffith et al. | |
| 2004/0229839 A1 | 11/2004 | Babu et al. | |
| 2004/0229840 A1 | 11/2004 | Bhat et al. | |
| 2006/0121312 A1 | 6/2006 | Yamada et al. | |
| 2006/0194144 A1 | 8/2006 | Sooriyakumaran et al. | |
| 2006/0281922 A1 | 12/2006 | Gao et al. | |
| 2007/0232635 A1 | 10/2007 | Chelliah et al. | |
| 2009/0318380 A1 | 12/2009 | Sofia et al. | |
| 2009/0323011 A1 | 12/2009 | He et al. | |
| 2009/0323012 A1 | 12/2009 | He et al. | |
| 2010/0035836 A1 | 2/2010 | Francom et al. | |
| 2010/0040804 A1 | 2/2010 | Zhang | |
| 2010/0096603 A1 | 4/2010 | Wang et al. | |
| 2010/0184942 A1 | 7/2010 | Chen et al. | |
| 2010/0186626 A1 | 7/2010 | Shin et al. | |
| 2011/0212994 A1 | 9/2011 | Clem et al. | |
| 2011/0216273 A1 | 9/2011 | He et al. | |
| 2011/0287927 A1 | 11/2011 | Grasset et al. | |
| 2011/0319459 A1 | 12/2011 | Gupta et al. | |
| 2012/0009147 A1 | 1/2012 | Cho et al. | |
| 2012/0020921 A1 | 1/2012 | Cho et al. | |
| 2012/0035115 A1 | 2/2012 | Manoharan et al. | |
| 2012/0070411 A1 | 3/2012 | Beigelman et al. | |
| 2012/0070415 A1 | 3/2012 | Beigelman et al. | |
| 2012/0071434 A1 | 3/2012 | Smith et al. | |
| 2012/0214735 A1 | 8/2012 | Bhuniya et al. | |
| 2012/0214762 A1 | 8/2012 | Staben et al. | |
| 2012/0219568 A1 | 8/2012 | Liu et al. | |
| 2012/0264649 A1 | 10/2012 | Bazan et al. | |
| 2013/0303669 A1 | 11/2013 | Morimoto et al. | |
| 2014/0038991 A1 | 2/2014 | Yu et al. | |
| 2014/0200215 A1 | 7/2014 | Buckman et al. | |

(Continued)

FOREIGN PATENT DOCUMENTS

| | | | |
|---|---|---|---|
| CN | 102000103 A | 4/2011 | |
| CN | 102286047 A | 12/2011 | |

(Continued)

OTHER PUBLICATIONS

U.S. Appl. No. 17/176,497, filed Feb. 16, 2016, Byun et al.
First Office Action and Search Report in Taiwan (ROC) Application 110104869 dated Jan. 24, 2022, 7 pages (3 pages of English Translation and 4 pages of Taiwan Office Action).
First Office Action and Search Report in Taiwan (ROC) Application 110105126 dated Jan. 6, 2022, 7 pages (3 pages of English Translation and 4 pages of Taiwan Office Action).
International Preliminary Report on Patentability received for PCT Application No. PCT/US2021/018169, dated Dec. 15, 2021, 20 pages.

(Continued)

*Primary Examiner* — Traviss C McIntosh, III
(74) *Attorney, Agent, or Firm* — Mintz, Levin, Cohn, Ferris, Glovsky and Popeo, P.C.

(57) ABSTRACT

The present disclosure describes methods of preparing carbanucleosides.

28 Claims, No Drawings

(56) References Cited

U.S. PATENT DOCUMENTS

| | | |
|---|---|---|
| 2014/0309413 A1 | 10/2014 | Rose et al. |
| 2015/0011497 A1 | 1/2015 | Beigelman et al. |
| 2015/0051167 A1 | 2/2015 | Wang et al. |
| 2015/0105341 A1 | 4/2015 | Beigelman et al. |
| 2015/0252265 A1 | 9/2015 | Archetti et al. |
| 2015/0274767 A1 | 10/2015 | Girijavallabhan et al. |
| 2015/0366887 A1 | 12/2015 | Blatt et al. |
| 2015/0366888 A1 | 12/2015 | Blatt et al. |
| 2016/0024107 A1 | 1/2016 | Clarke et al. |
| 2016/0053175 A1 | 2/2016 | Song et al. |
| 2016/0122374 A1 | 5/2016 | Chun et al. |
| 2016/0244668 A1 | 8/2016 | Saito et al. |
| 2016/0257657 A1 | 9/2016 | Wipf et al. |
| 2017/0071964 A1 | 3/2017 | Clarke et al. |
| 2017/0186964 A1 | 6/2017 | Cho et al. |
| 2018/0002366 A1 | 1/2018 | Girijavallabhan et al. |
| 2018/0044369 A1 | 2/2018 | Beigelman et al. |
| 2018/0079774 A1 | 3/2018 | Beigelman et al. |
| 2018/0226580 A1 | 8/2018 | Fitzgerald et al. |
| 2019/0185748 A1 | 6/2019 | Liao |
| 2019/0185754 A1 | 6/2019 | Archetti et al. |
| 2019/0241807 A1 | 8/2019 | Mizusaki et al. |
| 2021/0060051 A1 | 3/2021 | Schinazi et al. |
| 2021/0284669 A1* | 9/2021 | Chun .................. A61K 31/706 |
| 2021/0284670 A1 | 9/2021 | Chin et al. |
| 2021/0292348 A1 | 9/2021 | Byun et al. |

FOREIGN PATENT DOCUMENTS

| | | |
|---|---|---|
| CN | 102603836 A | 7/2012 |
| CN | 103709220 A | 4/2014 |
| CN | 104086612 A | 10/2014 |
| CN | 105646629 A | 6/2016 |
| CN | 105777580 A | 7/2016 |
| CN | 106518766 A | 3/2017 |
| CN | 106518767 A | 3/2017 |
| CN | 106892920 A | 6/2017 |
| CN | 107286190 A | 10/2017 |
| CN | 108276352 A | 7/2018 |
| CN | 109748921 A | 5/2019 |
| CN | 109748943 A | 5/2019 |
| CN | 109748944 A | 5/2019 |
| CN | 110215456 A | 9/2019 |
| CN | 110330540 A | 10/2019 |
| CN | 110724174 A | 1/2020 |
| CN | 110776512 A | 2/2020 |
| CN | 111620909 A | 9/2020 |
| DE | 2626792 A1 | 12/1977 |
| DE | 3528753 A1 | 2/1987 |
| DE | 4232852 A1 | 3/1994 |
| DE | 19934799 A1 | 2/2001 |
| DE | 10064823 A1 | 6/2002 |
| EP | 0284952 A2 | 10/1988 |
| EP | 0419944 A2 | 4/1991 |
| EP | 0458214 A1 | 11/1991 |
| EP | 0682098 A2 | 11/1995 |
| EP | 0924265 A2 | 6/1999 |
| EP | 1046631 A1 | 10/2000 |
| EP | 1170353 A2 | 1/2002 |
| EP | 1593713 A1 | 11/2005 |
| EP | 1975718 A2 | 10/2008 |
| EP | 1978077 A1 | 10/2008 |
| EP | 2098226 A1 | 9/2009 |
| EP | 2388069 A1 | 11/2011 |
| EP | 2778169 A1 | 9/2014 |
| EP | 2896678 A1 | 7/2015 |
| EP | 2980182 A1 | 2/2016 |
| FR | 2354774 A1 | 1/1978 |
| FR | 2669639 A1 | 5/1992 |
| IN | 167775 B | 12/1990 |
| JP | S5170794 A | 6/1976 |
| JP | S6286363 A | 4/1987 |
| JP | H0931092 A | 2/1997 |
| JP | H09328497 A | 12/1997 |
| JP | 2002326995 A | 11/2002 |
| JP | 2002326996 A | 11/2002 |
| JP | 2003246770 | 9/2003 |
| JP | 2004315613 A | 11/2004 |
| JP | 2005120172 A | 5/2005 |
| JP | 2006232875 A | 9/2006 |
| JP | 2008007634 A | 1/2008 |
| JP | 2012216832 A | 11/2012 |
| JP | 5295692 B2 | 9/2013 |
| JP | 2014145852 A | 8/2014 |
| JP | 2016132779 A | 7/2016 |
| JP | 2018044028 A | 3/2018 |
| JP | 2018203945 A | 12/2018 |
| KR | 1020120135501 A | 12/2012 |
| KR | 1020160098975 A | 8/2016 |
| KR | 1020160110899 A | 9/2016 |
| KR | 1020160110900 A | 9/2016 |
| KR | 1020190041918 A | 4/2019 |
| KR | 1020190076339 A | 7/2019 |
| NL | 7606413 A | 12/1977 |
| WO | 8807043 A1 | 9/1988 |
| WO | 9110671 A1 | 7/1991 |
| WO | 9201695 A1 | 2/1992 |
| WO | 9201696 A1 | 2/1992 |
| WO | 9214805 A1 | 9/1992 |
| WO | 9316075 A1 | 8/1993 |
| WO | 9614329 A1 | 5/1996 |
| WO | 9640705 A1 | 12/1996 |
| WO | 9816184 A2 | 4/1998 |
| WO | 9900399 A1 | 1/1999 |
| WO | 9914226 A2 | 3/1999 |
| WO | 9926933 A1 | 6/1999 |
| WO | 9926941 A1 | 6/1999 |
| WO | 9951565 A1 | 10/1999 |
| WO | 9961583 A2 | 12/1999 |
| WO | 0001381 A1 | 1/2000 |
| WO | 0032152 A2 | 6/2000 |
| WO | 0034276 A1 | 6/2000 |
| WO | 0063154 A1 | 10/2000 |
| WO | 0066604 A2 | 11/2000 |
| WO | 0100197 A2 | 1/2001 |
| WO | 0110842 A2 | 2/2001 |
| WO | 0114320 A1 | 3/2001 |
| WO | 0119841 A1 | 3/2001 |
| WO | 0121577 A2 | 3/2001 |
| WO | 0123357 A2 | 4/2001 |
| WO | 0147862 A1 | 7/2001 |
| WO | 0164642 A2 | 9/2001 |
| WO | 0177091 A2 | 10/2001 |
| WO | 0207516 A2 | 1/2002 |
| WO | 0234711 A1 | 5/2002 |
| WO | 0234736 A1 | 5/2002 |
| WO | 0239987 A2 | 5/2002 |
| WO | 02062766 A2 | 8/2002 |
| WO | 02094185 A2 | 11/2002 |
| WO | 02100415 A2 | 12/2002 |
| WO | 03039523 A2 | 5/2003 |
| WO | 03041649 A2 | 5/2003 |
| WO | 03049772 A2 | 6/2003 |
| WO | 03088908 A2 | 10/2003 |
| WO | 03090748 A1 | 11/2003 |
| WO | 03091262 A1 | 11/2003 |
| WO | 2004002999 A2 | 1/2004 |
| WO | 2004007472 A1 | 1/2004 |
| WO | 2004014312 A2 | 2/2004 |
| WO | 2004037159 A2 | 5/2004 |
| WO | 2004041752 A2 | 5/2004 |
| WO | 2004080966 A1 | 9/2004 |
| WO | 2004083177 A2 | 9/2004 |
| WO | 2004083263 A1 | 9/2004 |
| WO | 2004087153 A2 | 10/2004 |
| WO | 2004091499 A2 | 10/2004 |
| WO | 2004106356 A1 | 12/2004 |
| WO | 2004110350 A2 | 12/2004 |
| WO | 2005020885 A2 | 3/2005 |
| WO | 2005021568 A2 | 3/2005 |
| WO | 2005023771 A1 | 3/2005 |
| WO | 2005025515 A2 | 3/2005 |
| WO | 2005040135 A1 | 5/2005 |
| WO | 2005058832 A1 | 6/2005 |

(56) References Cited

FOREIGN PATENT DOCUMENTS

| | | |
|---|---|---|
| WO | 2005093476 A1 | 10/2005 |
| WO | 2005095544 A1 | 10/2005 |
| WO | 2005097052 A1 | 10/2005 |
| WO | 2005111099 A1 | 11/2005 |
| WO | 2006001463 A1 | 1/2006 |
| WO | 2006006490 A1 | 1/2006 |
| WO | 2006008438 A1 | 1/2006 |
| WO | 2006016101 A1 | 2/2006 |
| WO | 2006030193 A1 | 3/2006 |
| WO | 2006038594 A1 | 4/2006 |
| WO | 2006048634 A1 | 5/2006 |
| WO | 2006061094 A1 | 6/2006 |
| WO | 2006063717 A2 | 6/2006 |
| WO | 2006066074 A2 | 6/2006 |
| WO | 2006094347 A1 | 9/2006 |
| WO | 2006098380 A1 | 9/2006 |
| WO | 2006105440 A2 | 10/2006 |
| WO | 2006110656 A2 | 10/2006 |
| WO | 2006119800 A1 | 11/2006 |
| WO | 2006130217 A2 | 12/2006 |
| WO | 2007007588 A1 | 1/2007 |
| WO | 2007011759 A2 | 1/2007 |
| WO | 2007024021 A1 | 3/2007 |
| WO | 2007031185 A1 | 3/2007 |
| WO | 2007056143 A2 | 5/2007 |
| WO | 2007056170 A2 | 5/2007 |
| WO | 2007076034 A2 | 7/2007 |
| WO | 2007084667 A2 | 7/2007 |
| WO | 2007095188 A2 | 8/2007 |
| WO | 2007125320 A1 | 11/2007 |
| WO | 2007130783 A2 | 11/2007 |
| WO | 2008001195 A2 | 1/2008 |
| WO | 2008011557 A2 | 1/2008 |
| WO | 2008012555 A2 | 1/2008 |
| WO | 2008021388 A1 | 2/2008 |
| WO | 2008024364 A2 | 2/2008 |
| WO | 2008082601 A2 | 7/2008 |
| WO | 2008092006 A2 | 7/2008 |
| WO | 2008095040 A2 | 8/2008 |
| WO | 2008109177 A2 | 9/2008 |
| WO | 2008109180 A2 | 9/2008 |
| WO | 2008109181 A2 | 9/2008 |
| WO | 2008117047 A1 | 10/2008 |
| WO | 2008121360 A1 | 10/2008 |
| WO | 2008133966 A1 | 11/2008 |
| WO | 2008151437 A1 | 12/2008 |
| WO | 2009001097 A2 | 12/2008 |
| WO | 2009009951 A1 | 1/2009 |
| WO | 2009011228 A1 | 1/2009 |
| WO | 2009011229 A1 | 1/2009 |
| WO | 2009067409 A1 | 5/2009 |
| WO | 2009069095 A2 | 6/2009 |
| WO | 2009076593 A1 | 6/2009 |
| WO | 2009076618 A2 | 6/2009 |
| WO | 2009086192 A1 | 7/2009 |
| WO | 2009086201 A1 | 7/2009 |
| WO | 2009111653 A2 | 9/2009 |
| WO | 2009132123 A1 | 10/2009 |
| WO | 2009132135 A1 | 10/2009 |
| WO | 2009151921 A1 | 12/2009 |
| WO | 2009152095 A2 | 12/2009 |
| WO | 2010001174 A1 | 1/2010 |
| WO | 2010007116 A2 | 1/2010 |
| WO | 2010026153 A1 | 3/2010 |
| WO | 2010036407 A2 | 4/2010 |
| WO | 2010060952 A1 | 6/2010 |
| WO | 2010073126 A2 | 7/2010 |
| WO | 2010084115 A2 | 7/2010 |
| WO | 2010108135 A1 | 9/2010 |
| WO | 2010108140 A1 | 9/2010 |
| WO | 2010145778 A1 | 12/2010 |
| WO | 2011005860 A2 | 1/2011 |
| WO | 2011015037 A1 | 2/2011 |
| WO | 2011016430 A1 | 2/2011 |
| WO | 2011031896 A2 | 3/2011 |
| WO | 2011032169 A2 | 3/2011 |
| WO | 2011035231 A1 | 3/2011 |
| WO | 2011035250 A1 | 3/2011 |
| WO | 2011035842 A1 | 3/2011 |
| WO | 2011036557 A1 | 3/2011 |
| WO | 2011038207 A1 | 3/2011 |
| WO | 2011057214 A2 | 5/2011 |
| WO | 2011086075 A1 | 7/2011 |
| WO | 2011097300 A1 | 8/2011 |
| WO | 2011100131 A2 | 8/2011 |
| WO | 2011109799 A1 | 9/2011 |
| WO | 2011119869 A1 | 9/2011 |
| WO | 2011146401 A1 | 11/2011 |
| WO | 2011150288 A1 | 12/2011 |
| WO | 2011156632 A2 | 12/2011 |
| WO | 2012012465 A1 | 1/2012 |
| WO | 2012012776 A1 | 1/2012 |
| WO | 2012031539 A1 | 3/2012 |
| WO | 2012034626 A1 | 3/2012 |
| WO | 2012037038 A1 | 3/2012 |
| WO | 2012040124 A1 | 3/2012 |
| WO | 2012040126 A1 | 3/2012 |
| WO | 2012040127 A1 | 3/2012 |
| WO | 2012068340 A2 | 5/2012 |
| WO | 2012083048 A2 | 6/2012 |
| WO | 2012087596 A1 | 6/2012 |
| WO | 2012088155 A1 | 6/2012 |
| WO | 2012088438 A1 | 6/2012 |
| WO | 2012092471 A2 | 7/2012 |
| WO | 2012121973 A1 | 9/2012 |
| WO | 2012128944 A1 | 9/2012 |
| WO | 2012139028 A2 | 10/2012 |
| WO | 2012142075 A1 | 10/2012 |
| WO | 2012142085 A1 | 10/2012 |
| WO | 2012142523 A2 | 10/2012 |
| WO | 2012160392 A1 | 11/2012 |
| WO | 2013000855 A1 | 1/2013 |
| WO | 2013007586 A1 | 1/2013 |
| WO | 2013030288 A1 | 3/2013 |
| WO | 2013033270 A2 | 3/2013 |
| WO | 2013040492 A2 | 3/2013 |
| WO | 2013040568 A1 | 3/2013 |
| WO | 2013044030 A1 | 3/2013 |
| WO | 2013056132 A2 | 4/2013 |
| WO | 2013072466 A1 | 5/2013 |
| WO | 2013087765 A1 | 6/2013 |
| WO | 2013090420 A2 | 6/2013 |
| WO | 2013096679 A1 | 6/2013 |
| WO | 2013096680 A1 | 6/2013 |
| WO | 2013101552 A1 | 7/2013 |
| WO | 2013135339 A2 | 9/2013 |
| WO | 2013138236 A1 | 9/2013 |
| WO | 2013142124 A1 | 9/2013 |
| WO | 2013142157 A1 | 9/2013 |
| WO | 2013142159 A1 | 9/2013 |
| WO | 2013142525 A1 | 9/2013 |
| WO | 2013147795 A1 | 10/2013 |
| WO | 2013151975 A1 | 10/2013 |
| WO | 2013182262 A1 | 12/2013 |
| WO | 2014005125 A2 | 1/2014 |
| WO | 2014008236 A1 | 1/2014 |
| WO | 2014015936 A1 | 1/2014 |
| WO | 2014026198 A1 | 2/2014 |
| WO | 2014031872 A2 | 2/2014 |
| WO | 2014035140 A2 | 3/2014 |
| WO | 2014048998 A1 | 4/2014 |
| WO | 2014057095 A1 | 4/2014 |
| WO | 2014058801 A1 | 4/2014 |
| WO | 2014059901 A1 | 4/2014 |
| WO | 2014059902 A1 | 4/2014 |
| WO | 2014090369 A1 | 6/2014 |
| WO | 2014100498 A1 | 6/2014 |
| WO | 2014100505 A1 | 6/2014 |
| WO | 2014102077 A1 | 7/2014 |
| WO | 2014124458 A1 | 8/2014 |
| WO | 2014134127 A1 | 9/2014 |
| WO | 2014134251 A1 | 9/2014 |
| WO | 2014149164 A1 | 9/2014 |
| WO | 2014160012 A2 | 10/2014 |

(56) References Cited

FOREIGN PATENT DOCUMENTS

| | | |
|---|---|---|
| WO | 2014209979 A1 | 12/2014 |
| WO | 2015003146 A1 | 1/2015 |
| WO | 2015006280 A1 | 1/2015 |
| WO | 2015016187 A1 | 2/2015 |
| WO | 2015024120 A1 | 2/2015 |
| WO | 2015031710 A1 | 3/2015 |
| WO | 2015038596 A1 | 3/2015 |
| WO | 2015046827 A1 | 4/2015 |
| WO | 2015051169 A2 | 4/2015 |
| WO | 2015061742 A2 | 4/2015 |
| WO | 2015069939 A1 | 5/2015 |
| WO | 2015089511 A2 | 6/2015 |
| WO | 2015118898 A1 | 8/2015 |
| WO | 2015120237 A2 | 8/2015 |
| WO | 2015129672 A1 | 9/2015 |
| WO | 2015143712 A1 | 10/2015 |
| WO | 2015148746 A1 | 10/2015 |
| WO | 2015148869 A1 | 10/2015 |
| WO | 2015160251 A1 | 10/2015 |
| WO | 2015196118 A1 | 12/2015 |
| WO | 2015196128 A2 | 12/2015 |
| WO | 2015196130 A2 | 12/2015 |
| WO | 2015198915 A1 | 12/2015 |
| WO | 2015200205 A1 | 12/2015 |
| WO | 2015200219 A1 | 12/2015 |
| WO | 2016010026 A1 | 1/2016 |
| WO | 2016018697 A1 | 2/2016 |
| WO | 2016029186 A1 | 2/2016 |
| WO | 2016031406 A1 | 3/2016 |
| WO | 2016041877 A1 | 3/2016 |
| WO | 2016066582 A1 | 5/2016 |
| WO | 2016069827 A1 | 5/2016 |
| WO | 2016069975 A1 | 5/2016 |
| WO | 2016070952 A1 | 5/2016 |
| WO | 2016074762 A1 | 5/2016 |
| WO | 2016096076 A1 | 6/2016 |
| WO | 2016100441 A1 | 6/2016 |
| WO | 2016100569 A1 | 6/2016 |
| WO | 2016107664 A1 | 7/2016 |
| WO | 2016115222 A1 | 7/2016 |
| WO | 2016116124 A1 | 7/2016 |
| WO | 2016116254 A1 | 7/2016 |
| WO | 2016116508 A1 | 7/2016 |
| WO | 2016117271 A1 | 7/2016 |
| WO | 2016145142 A1 | 9/2016 |
| WO | 2016148170 A1 | 9/2016 |
| WO | 2016152340 A1 | 9/2016 |
| WO | 2016161176 A1 | 10/2016 |
| WO | 2016162644 A1 | 10/2016 |
| WO | 2016170948 A1 | 10/2016 |
| WO | 2016172631 A2 | 10/2016 |
| WO | 2016178876 A2 | 11/2016 |
| WO | 2016184361 A1 | 11/2016 |
| WO | 2016192902 A1 | 12/2016 |
| WO | 2017005673 A1 | 1/2017 |
| WO | 2017019817 A1 | 2/2017 |
| WO | 2017019822 A1 | 2/2017 |
| WO | 2017019830 A1 | 2/2017 |
| WO | 2017023894 A1 | 2/2017 |
| WO | 2017024310 A1 | 2/2017 |
| WO | 2017027646 A1 | 2/2017 |
| WO | 2017032840 A1 | 3/2017 |
| WO | 2017041893 A1 | 3/2017 |
| WO | 2017045612 A1 | 3/2017 |
| WO | 2017045615 A1 | 3/2017 |
| WO | 2017045616 A1 | 3/2017 |
| WO | 2017045740 A1 | 3/2017 |
| WO | 2017049060 A1 | 3/2017 |
| WO | 2017058807 A1 | 4/2017 |
| WO | 2017059357 A1 | 4/2017 |
| WO | 2017066781 A1 | 4/2017 |
| WO | 2017066782 A1 | 4/2017 |
| WO | 2017066791 A1 | 4/2017 |
| WO | 2017066793 A1 | 4/2017 |
| WO | 2017066797 A1 | 4/2017 |
| WO | 2017068875 A1 | 4/2017 |
| WO | 2017073931 A1 | 5/2017 |
| WO | 2017073932 A1 | 5/2017 |
| WO | 2017073933 A1 | 5/2017 |
| WO | 2017091767 A2 | 6/2017 |
| WO | 2017093214 A1 | 6/2017 |
| WO | 2017097401 A1 | 6/2017 |
| WO | 2017153186 A1 | 9/2017 |
| WO | 2017156262 A1 | 9/2017 |
| WO | 2017161028 A1 | 9/2017 |
| WO | 2017165489 A1 | 9/2017 |
| WO | 2017184668 A1 | 10/2017 |
| WO | 2017205980 A1 | 12/2017 |
| WO | 2017207993 A1 | 12/2017 |
| WO | 2018015323 A2 | 1/2018 |
| WO | 2018031818 A2 | 2/2018 |
| WO | 2018065356 A1 | 4/2018 |
| WO | 2018067615 A1 | 4/2018 |
| WO | 2018098206 A1 | 5/2018 |
| WO | 2018106818 A1 | 6/2018 |
| WO | 2018106820 A1 | 6/2018 |
| WO | 2018110529 A1 | 6/2018 |
| WO | 2018116901 A1 | 6/2018 |
| WO | 2018119263 A1 | 6/2018 |
| WO | 2018138685 A2 | 8/2018 |
| WO | 2018169946 A1 | 9/2018 |
| WO | 2018175746 A1 | 9/2018 |
| WO | 2018183635 A1 | 10/2018 |
| WO | 2018184590 A1 | 10/2018 |
| WO | 2018189134 A1 | 10/2018 |
| WO | 2018204198 A1 | 11/2018 |
| WO | 2018208667 A1 | 11/2018 |
| WO | 2018213185 A1 | 11/2018 |
| WO | 2018218171 A1 | 11/2018 |
| WO | 2018218281 A1 | 12/2018 |
| WO | 2018222172 A1 | 12/2018 |
| WO | 2018226976 A1 | 12/2018 |
| WO | 2018237194 A1 | 12/2018 |
| WO | 2019014247 A1 | 1/2019 |
| WO | 2019018185 A1 | 1/2019 |
| WO | 2019051269 A1 | 3/2019 |
| WO | 2019052935 A1 | 3/2019 |
| WO | 2019053696 A1 | 3/2019 |
| WO | WO-2019053696 A1 * | 3/2019 ......... A61K 31/7064 |
| WO | 2019084271 A1 | 5/2019 |
| WO | 2019086400 A1 | 5/2019 |
| WO | 2019092171 A1 | 5/2019 |
| WO | 2019098109 A1 | 5/2019 |
| WO | 2019125974 A1 | 6/2019 |
| WO | 2019129059 A1 | 7/2019 |
| WO | 2019133712 A1 | 7/2019 |
| WO | 2019154953 A1 | 8/2019 |
| WO | 2019154956 A1 | 8/2019 |
| WO | 2019173682 A1 | 9/2019 |
| WO | 2019195056 A1 | 10/2019 |
| WO | 2019215076 A1 | 11/2019 |
| WO | 2019218797 A1 | 11/2019 |
| WO | 2020032152 A1 | 2/2020 |
| WO | 2020033413 A2 | 2/2020 |
| WO | 2021167882 A1 | 8/2021 |
| WO | 2021168004 A1 | 8/2021 |
| WO | 2021168008 A1 | 8/2021 |
| WO | 2021168038 A1 | 8/2021 |
| WO | 2021175296 A1 | 9/2021 |

OTHER PUBLICATIONS

International Search Report and Written Opinion received for PCT Application No. PCT/US2021/018169, dated Apr. 26, 2021, 19 pages.

International Search Report and Written Opinion received for PCT Application No. PCT/US2021/018410, dated May 10, 2021, 11 pages.

International Search Report and Written Opinion received for PCT Application No. PCT/US2021/018415, dated May 11, 2021, 14 pages.

(56) References Cited

OTHER PUBLICATIONS

International Search Report and Written Opinion received for PCT Application No. PCT/US2021/018458, dated May 18, 2021, 17 pages.

Office Action and Search Report in Taiwan Application No. 110105140, dated Dec. 7, 2021, 7 pages (3 pages of English Translation and 4 pages of Taiwan Office Action).

Office Action and Search Report in Taiwan Application No. 110105397, dated Dec. 3, 2021, 11 pages (5 pages of English Translation and 6 pages of Taiwan Office Action).

Cockerill et al. (2019) "State of the Art in Respiratory Syncytial Virus Drug Discovery and Development", Journal of Medicinal Chemistry, 62(7):3206-3227.

Colombo et al. (1985) "Asymetric Dihydroxylations via Chiral Oxazolidines", Tetrahedron Letters, 26(44):5459-5462.

Feng et al. (Apr. 2014) "Inhibition of Hepatitis C Virus Replication by GS-6620, a Potent C-Nucleoside Monophosphate Prodrug", Antimicrobial Agents and Chemotherapy, 58(4):1930-1942.

Griffon et al. (2001) "Synthesis and Antiproliferative Activity of Some 4'-C-Hydroxymethyl-A- and -B-D-Arabino-Pentofuranosyl Pyrimidine Nucleosides", Nucleosides, Nucleotides & Nucleic Acids, 20(4-7):649-652.

Griffon et al. (2006) "Synthesis and Biological Evaluation of Some 4'-C-(Hydroxymethyl)-α- and -β-D-Arabinofuranosyl Pyrimidine and Adenine Nucleosides", Collection of Czechoslovak Chemical Communications, 71(7):1063-1087.

Koshkin et al. (Apr. 2, 1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.

Leisvuori Anna (Sep. 2015) "Prodrug Strategies of Antiviral Nucleotides: Studies on Enzymatically and Thermally Removable Phosphate Protecting Groups", University of Turku, Turku, Finland, 86 pages.

Musich et al. (1978) "Synthesis of Anthopleurine, The Alarm Pheromone from Anthopleura Elegantissima", Journal of the American Chemical Society, 100(15):4865-4872.

Overend et al. (1970) "Branched Chain Sugars Part 12 Branched Sugars Derived from Methyl 2 3 o iso Propylidene Beta I erythro Pento Pyranosid 4 ulose and a Synthesis of I apiose", Carbohydrate Research, 15(2):185-195.

Patil et al. (Jul. 25, 1994) "4-Aza-7,9-Dideazaadenosine, a New Cytotoxic Synthetic C-Nucleoside Analogue of Adenosine", Tetrahedron Letters, 35(30):5339-5342.

Patil et al. (Jul.-Aug. 1994) "Synthesis of Pyrrolo[2,1-f][1,2,4]triazine Congeners of Nucleic Acid Purines via the N-Amination of 2-Substituted Pyrroles", Journal of Heterocyclic Chemistry, 31(4):781-786.

Shrestha et al. (Nov. 7, 2011) "Synthesis and Properties of a Bridged Nucleic Acid with a Perhydro-1,2-oxazin-3-one Ring", Journal of Organic Chemistry, 76(24):9891-9899.

Timpe et al. (Jan. 1975) "3-desoxyhex-2-enono-1,4-lactone aus D-hexofuran(osid)-urono-6,3-lactonen", Carbohydrate Research, 39(1):53-60.

Waga et al. (Jan. 26, 1993) "Synthesis of 4'-C-Methylnucleosides", Bioscience, Biotechnology, Biochemistry, 57(9):1433-1438.

Wenska et al. (Nov. 8, 2006) "Synthesis of Conformationally Constrained 2'-N,4'-C-Ethylene-Bridged Adenosine (aza-ENA-A)", Heterocycles, 73(1):303-324.

Youssefyeh et al. (1977) "Synthetic Routes to 4'-hydroxymethylnucleosides", Tetrahedron Letters, 18(5):435-438.

European Patent Office Communication for EP Application No. 21710378.7, dated Sep. 27, 2022, 3 pages.

European Patent Office Communication for EP Application No. 21712279.5, dated Sep. 28, 2022, 3 pages.

International Search Report and Written Opinion for PCT International Application No. PCT/US2022/024784, dated Jul. 15, 2022, 8 pages.

International Search Report and Written Opinion for PCT International Application No. PCT/US2022/071736, dated Jul. 21, 2022, 14 pages.

International Preliminary Report on Patentability for PCT Application No. PCT/US2021/018415, dated Sep. 1, 2022, 9 pages.

International Preliminary Report on Patentability for PCT Application No. PCT/US2021/018458, dated Sep. 1, 2022, 12 pages.

Non-Final Office Action for U.S. Appl. No. 17/176,497 dated Jul. 27, 2022, 7 pages.

Non Final Office Action for U.S. Appl. No. 17/178,463 dated Jan. 18, 2023, 11 pages.

Notice of Allowance in Taiwan (ROC) Application No. 110104869, dated Sep. 30, 2022, 3 pages.

Notice of Allowance in Taiwan (ROC) Application No. 110105126, dated Nov. 22, 2022, 3 pages.

Xie et al. (2021) "Weinreb Amide Approach to the Practical Synthesis of a Key Remdesivir Intermediate", The Journal of Organic Chemistry, 86(7):5065-5072.

CAPLUS Chem Abs Acc. No. 2015:832846 Document 162:643613.

\* cited by examiner

METHODS OF PREPARING CARBANUCLEOSIDES USING AMIDES

CROSS-REFERENCES TO RELATED APPLICATIONS

This application claims priority to U.S. Provisional Application No. 63/175,724, filed Apr. 16, 2021, which is incorporated herein in its entireties for all purposes.

BACKGROUND

The compound 7-((3S,4R)-3,4-bis(benzyloxy)-5,5-bis((benzyloxy)methyl)tetrahydrofuran-2-yl)pyrrolo[2,1-f][1,2,4]triazin-4-amine and substituted compounds thereof are important synthetic intermediates (see, for example, PCT/US2021/018458, PCT/US2021/018169 and PCT/US2021/018415). There continues to be a need for improved methods of preparing such intermediates, and other carbanucleosides.

BRIEF SUMMARY

In one embodiment, the present disclosure provides a method of preparing a compound of Formula (II-a) or Formula (II-b):

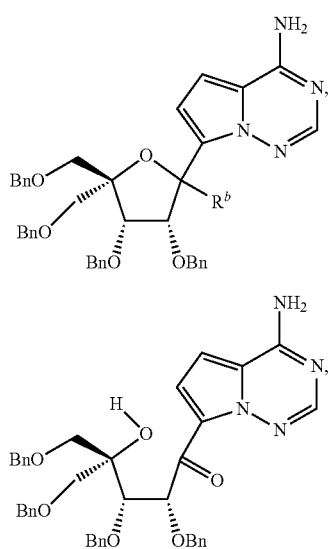

comprising:
(a) preparing a first input mixture, wherein the first input mixture comprises an amine protecting agent, a first base, a metalating agent, and a compound of Formula (IV):

to provide a first output mixture; and
(b) preparing a second input mixture comprising the first output mixture and a compound of Formula (V) to provide a second output mixture comprising the compound of Formula (II-a) or Formula (II-b), wherein the compound of Formula (V) has the structure:

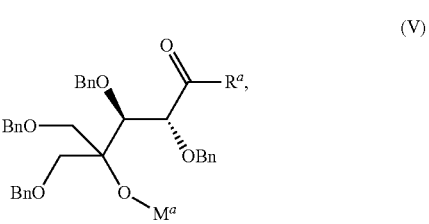

wherein
$R^a$ is

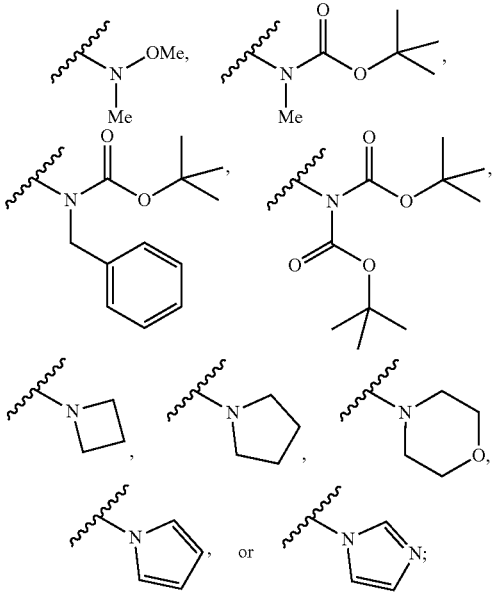

$M^a$ is Li or $MgX^a$;
$X^a$ is Cl, Br, or I;
$R^b$ is hydrogen or —OH; and
$X^b$ is Cl, Br, or I.

In another embodiment, the present disclosure provides a method of preparing a compound of Formula (II-a) or Formula (II-b):

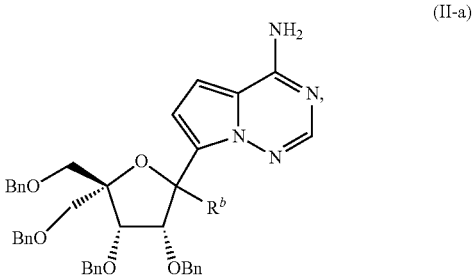

-continued (II-b)

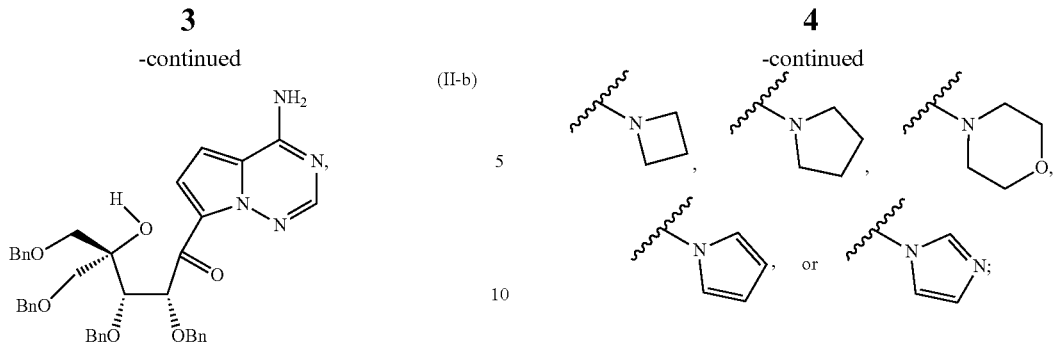

comprising:
(a) preparing a first input mixture in a first reactor, wherein the first input mixture comprises an amine protecting agent, a first base, a metalating agent, and a compound of Formula (IV):

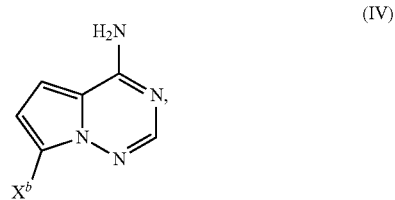

(IV)

wherein the first reactor provides a first output mixture; and
(b) adding the first output mixture and a compound of Formula (V) to form a second input mixture in a second reactor, wherein the compound of Formula (V) has the structure:

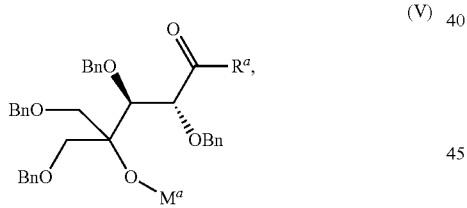

(V)

wherein
$R^a$ is

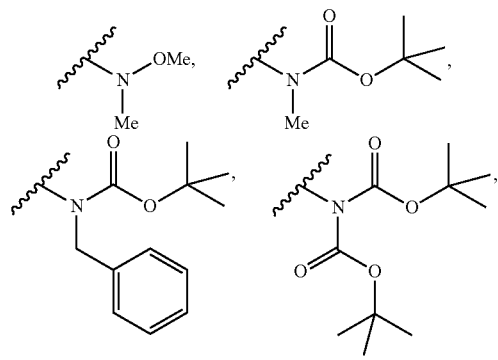

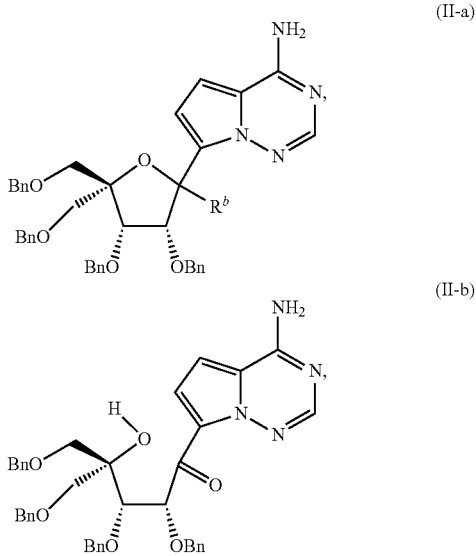

$M^a$ is Li or $MgX^a$;
$X^a$ is Cl, Br, or I;
$R^b$ is hydrogen or —OH;
$X^b$ is Cl, Br, or I; and
the second reactor provides a second output mixture comprising the compound of Formula (II-a) or Formula (II-b).

DETAILED DESCRIPTION

I. General

The present disclosure describes methods of preparing carbanucleosides. The methods described herein can relate to efficient, scalable processes that can be performed at any scale. In
some embodiments, the method comprises preparing the compound of Formula (II-a) or Formula (II-b):

(II-a)

(II-b)

from the compound of Formula (V):

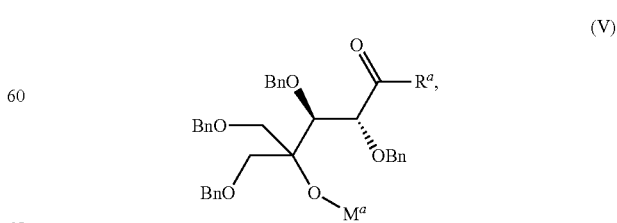

(V)

wherein $R^a$, $R^b$, and $M^a$ are as defined herein.

II. Definitions

"About" when referring to a value includes the stated value +/−10% of the stated value. For example, about 50% includes a range of from 45% to 55%, while about 20 molar equivalents includes a range of from 18 to 22 molar equivalents. Accordingly, when referring to a range, "about" refers to each of the stated values +/−10% of the stated value of each end of the range. For instance, a ratio of from about 1 to about 3 (weight/weight) includes a range of from 0.9 to 3.3.

"Input mixture" as used herein refers to a mixture of one or more reagents and/or solvents that enters a reactor.

"Output mixture" as used herein refers to a mixture of one or more reagents and/or solvents that exits a reactor.

"Reactor" refers to a vessel to which chemicals and reagents are added as an input mixture, and configured so that conversion of the chemicals, reagents, and other dependent variables are performed within the reactor. Each reactor can separately be a round-bottom flask, a batch reactor, a continuous flow reactor, a plug flow reactor, a continuous tubular reactor, a continuous stirred tank reactor, a mixed flow reactor, a semi-batch reactor, or combinations thereof. One or more reactors can be used in the method of the present disclosure. When multiple reactors are present the reactors can be of the same or different types of reactors.

"Catalyst" refers to a chemical reactant that increases the rate of a reaction without itself being consumed.

"Lewis acid" refers to a chemical group capable of accepting an electron pair from a second chemical group capable of donating an electron pair. Lewis acids can be inorganic compounds including, but not limited to, boron salts, such as boron trifluoride, or aluminum salts, such as aluminum trichloride; organic compound salts, such as trimethylsilyl trifluoromethanesulfonate (trimethylsilyl triflate or TMSOTf); or metal complexes containing organic and/or inorganic ligands, such as indium(III) chloride or dichlorodiisopropoxytitanium(IV). Exemplary Lewis acids include, but are not limited to, boron trifluoride diethyl etherate ($BF_3 \cdot Et_2O$), trimethylsilyl trifluoromethanesulfonate (trimethylsilyl triflate or TMSOTf), $TiCl_4$, $SnCl_4$, and $FeCl_3$.

"Bronsted acid," "Brønsted acid," or "Brønsted-Lowry acid" refers to an acid capable of donating a proton and forming the conjugate base. Examples of Bronsted acids include, but are not limited to, inorganic acids such as hydrogen chloride, hydrogen bromide, hydrogen iodide, hydrogen tetrafluoroborate, and sulfuric acid; and organic acids, e.g., carboxylic acids such as acetic acid and trifluoroacetic acid (TFA), or sulfonic acids such as p-toluenesulfonic acid and trifluoromethanesulfonic acid. Exemplary Bronsted acids include, but are not limited to, formic acid, acetic acid, dichloroacetic acid, and trifluoroacetic acid.

An "inorganic acid" or "mineral acid" is an acid derived from one or more inorganic compounds. Inorganic acids form hydrogen ions and the conjugate base when dissolved in water. Exemplary inorganic acids include, but are not limited to, hydrochloric acid and phosphoric acid.

An "organic acid" is an organic compound, a chemical compound containing a carbon-hydrogen bond, that has an acidic moiety. Organic acids include, but are not limited to, alkanecarboxylic acids, whose acidity is associated with their carboxyl group —COOH, and arylsulfonic acids, containing the group —$SO_2OH$. Exemplary organic acids include, but are not limited to, acetic acid and p-toluenesulfonic acid.

"Protecting group" refers to a moiety of a compound that masks or alters the properties of a functional group or the properties of the compound as a whole. The chemical substructure of a protecting group varies widely. One function of a protecting group is to serve as an intermediate in the synthesis of a desired compound. Chemical protecting groups and strategies for protection/deprotection are well known in the art. See also Protective Groups in Organic Chemistry, Peter G. M. Wuts and Theodora W. Greene, 4th Ed., 2006. Protecting groups are often utilized to mask the reactivity of certain functional groups, to assist in the efficiency of desired chemical reactions, e.g., making and breaking chemical bonds in an ordered and planned fashion. "Amine protecting group" refers to a protecting group useful for protecting amines bearing at least one uncharged hydrogen.

A "protecting agent" is a chemical reactant that is capable of effecting attachment of a protecting group. An "amine protecting agent" is a reactant capable of effecting attachment of an amine protecting group onto an amine.

"Metalating agent" is a chemical reactant that is capable of effecting the transfer of an organic ligand from a compound, wherein the ligand has a carbon bound to a metal atom on the compound.

"Reducing agent" refers to an agent capable of reducing an atom from a higher oxidation state to a lower oxidation state. Reducing agents can include, but are not limited to, zinc, iron, Raney nickel, sodium sulfide, sodium dithionite, ammonium sulfide, palladium on carbon, silanes, and hydrogen donors such as lithium aluminum hydride, sodium borohydride and sodiumtriacetoxyborohydride.

III. Methods of Preparing

Provided herein are methods of preparing a compound of Formula (II-a) or Formula (II-b) at various scales, such as multigram or kilogram scale. In some embodiments, the present disclosure provides a method of preparing a compound of Formula (II-a) or Formula (II-b):

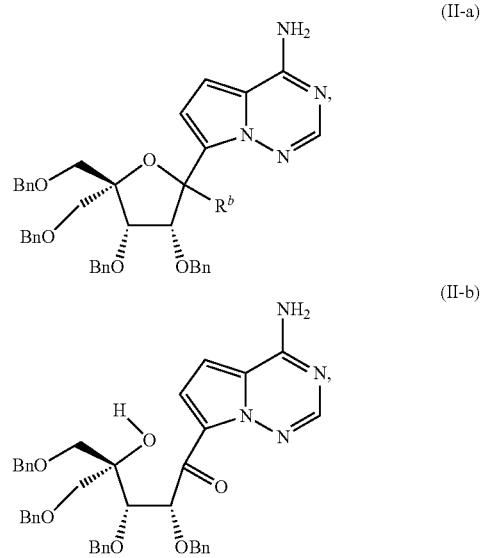

comprising:

(a) preparing a first input mixture, wherein the first input mixture comprises an amine protecting agent, a first base, a metalating agent, and a compound of Formula (IV):

to provide a first output mixture; and (b) preparing a second input mixture comprising the first output mixture and a compound of Formula (V) to provide a second output mixture comprising the compound of Formula (II-a) or Formula (II-b), wherein the compound of Formula (V) has the structure:

(V)

wherein
$R^a$ is $M^a$ is Li or MgX$^a$;
$X^a$ is Cl, Br, or I;
$R^b$ is hydrogen or —OH; and
$X^b$ is Cl, Br, or I.

In some embodiments, the present disclosure provides a method of preparing a compound of Formula (II-a) or Formula (II-b):

(II-a)

(II-b)

comprising:
(a) preparing a first input mixture in a first reactor, wherein the first input mixture comprises an amine protecting agent, a first base, a metalating agent, and a compound of Formula (IV):

(IV)

wherein the first reactor provides a first output mixture; and (b) adding the first output mixture and a compound of Formula (V) to form a second input mixture in a second reactor, wherein the compound of Formula (V) has the structure:

(V)

wherein
$R^a$ is

-continued

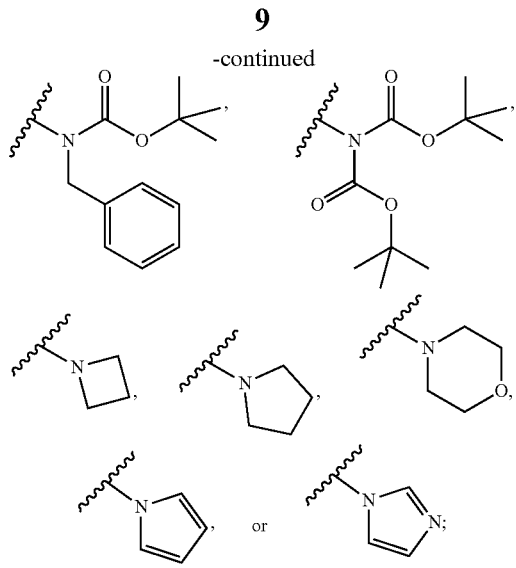

$M^a$ is Li or $MgX^a$;
$X^a$ is Cl, Br, or I;
$R^b$ is hydrogen or —OH;
$X^b$ is Cl, Br, or I; and the second reactor provides a second output mixture comprising the compound of Formula (II-a) or Formula (II-b).

In some embodiments, the present disclosure provides a method of preparing a compound of Formula (II-a) or Formula (II-b):

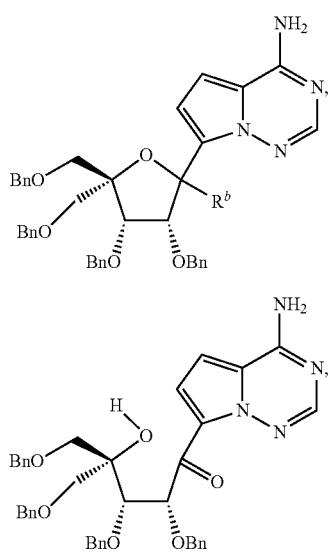

comprising:
(a) reacting a first input mixture to provide a first output mixture; and
(b) reacting the first output mixture with a compound of Formula (V) to provide the compound of Formula (II-a) or Formula (II-b);

wherein the first input mixture comprises an amine protecting agent, a first base, a metalating agent, and a compound of Formula (IV):

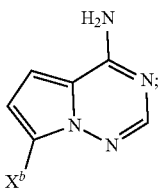

and wherein the compound of Formula (V) is:

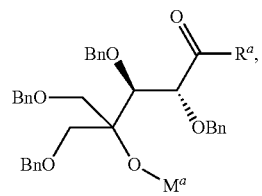

wherein
$R^a$ is

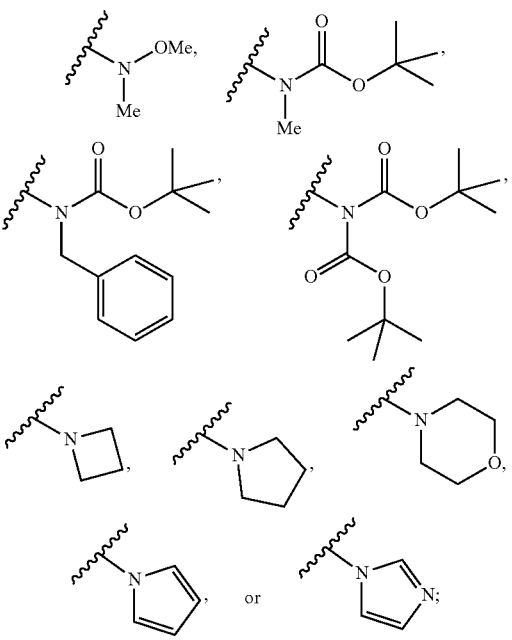

$M^a$ is Li or $MgX^a$;
$X^a$ is Cl, Br, or I; $R^b$ is hydrogen or —OH; and $X^b$ is Cl, Br, or I.

In some embodiments, $X^a$ is Cl, Br, or I. In some embodiments, $X^a$ is Br or I. In some embodiments, $X^a$ is Cl. In some embodiments, $X^a$ is Br. In some embodiments, $X^a$ is I.

In some embodiments, $M^a$ is Li or $MgX^a$. In some embodiments, $M^a$ is Li. In some embodiments, $M^a$ is $MgX^a$. In some embodiments, $M^a$ is MgCl. In some embodiments, $M^a$ is MgBr. In some embodiments, $M^a$ is MgI.

In some embodiments, $X^b$ is Cl, Br, or I. In some embodiments, $X^b$ is Br or I. In some embodiments, $X^b$ is Cl. In some embodiments, $X^b$ is Br. In some embodiments, $X^b$ is I.

In some embodiments, the compound of Formula (IV) has the structure:

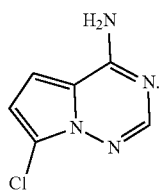

In some embodiments, the compound of Formula (IV) has the structure:

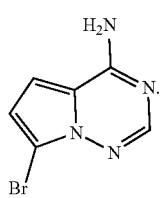 [SMILES: Nc1ncnn2c(Br)ccc12]

In some embodiments, the compound of Formula (IV) has the structure:

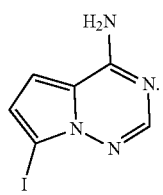

In some embodiments, $R^a$ is

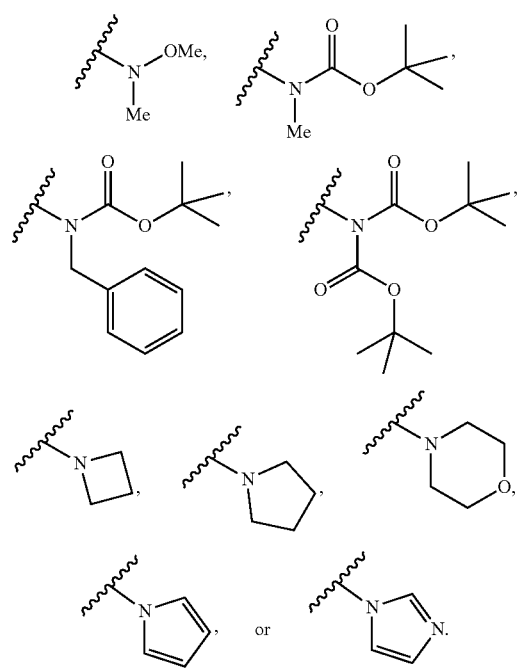

In some embodiments, $R^a$ is

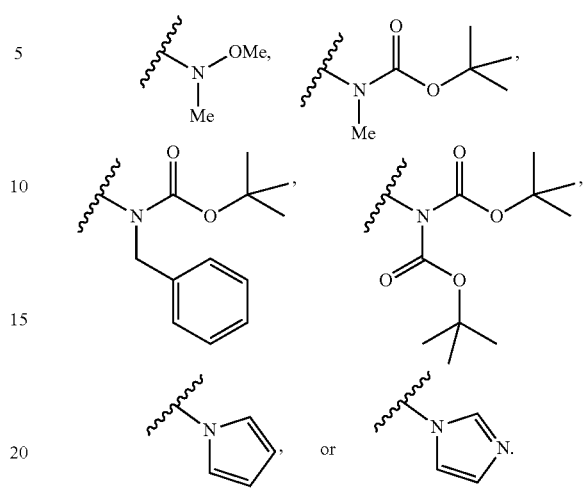

In some embodiments, $R^a$ is

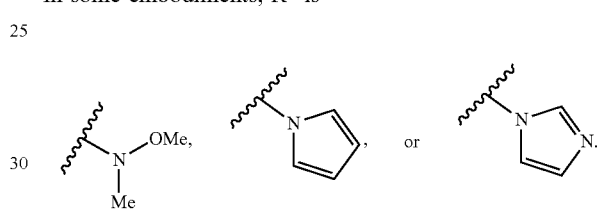

In some embodiments, $R^a$ is

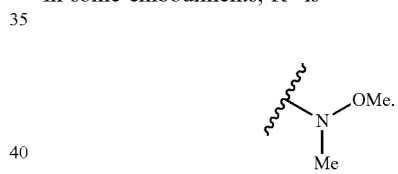

In some embodiments, the compound of Formula (V) has the structure:

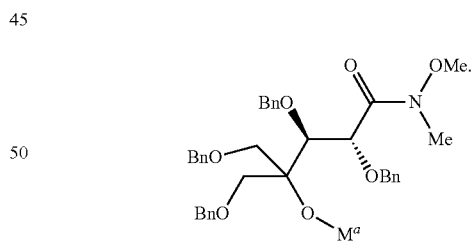

In some embodiments, the compound of Formula (V) has the structure:

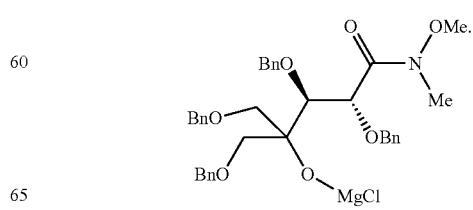

In some embodiments, the compound of Formula (V) has the structure:

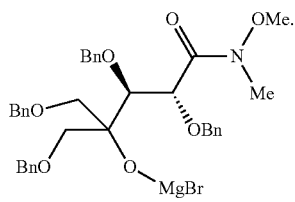

In some embodiments, the compound of Formula (V) has the structure:

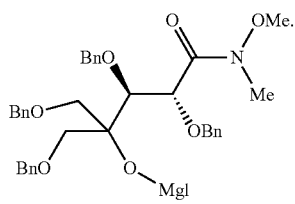

In some embodiments, $R^b$ is hydrogen. In some embodiments, $R^b$ is —OH.

In some embodiments, the compound of Formula (II-a) or Formula (II-b) has the structure:

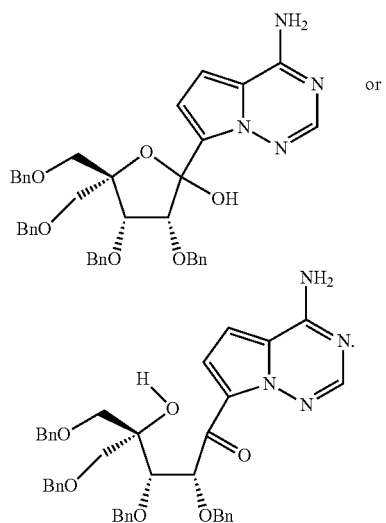

In some embodiments, the compound of Formula (II-a) has the structure:

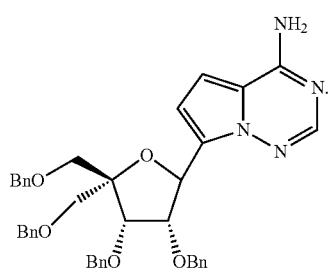

In some embodiments, the compound of Formula (II-a) has the structure:

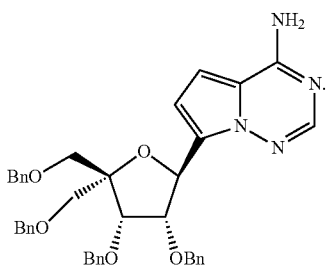

Any suitable amine protecting agent known in the art can be used in preparing the compound of Formula (II-a) or Formula (II-b). In some embodiments, the amine protecting agent is an anhydride, a silyl halide, or a silyl trifluoromethanesulfonate. Suitable anhydrides include, but are not limited to, trifluoroacetic anhydride and di(tert-butyl) dicarbonate. Silyl halides include, but are not limited to, trimethylsilyl halide (TMS-$X^4$), triethylsilyl halide (TES-$X^4$), triisopropylsilyl halide (TIPS-$X^4$), tert-butyldimethylsilyl halide (TBDMS-$X^4$), tert-butyldiphenylsilyl halide (TBDPS-$X^4$), triphenylsilyl halide (TPS-$X^4$), 1,2-bis(halodimethylsilyl)ethane ($X^4Me_2SiCH_2$-$CH_2SiMe_2X^4$), wherein $X^4$ is Cl, Br, or I. Silyl trifluoromethanesulfonates include, but are not limited to, trimethylsilyl trifluoromethanesulfonate (TMSOTf), triethylsilyl trifluoromethanesulfonate (TESOTf), triisopropylsilyl trifluoromethanesulfonate, tert-butyldimethylsilyl trifluoromethanesulfonate (TBDMSOTf), tert-butyldiphenylsilyl trifluoromethanesulfonate (TBDPSOTf), and triphenylsilyl trifluoromethanesulfonate. In some embodiments, the amine protecting agent is trifluoroacetic anhydride, di(tert-butyl) dicarbonate, trimethylsilyl chloride (TMSCl), triethylsilyl chloride (TESCl), triisopropylsilyl chloride, tert-butyldimethylsilyl chloride (TBDMSCl), tert-butyldiphenylsilyl chloride (TBDPSCl), triphenylsilyl chloride, or 1,2-bis (chlorodimethylsilyl)ethane. In some embodiments, the amine protecting agent is trimethylsilyl chloride (TMSCl).

Any suitable first base capable of deprotonating the compound of Formula (IV) can be used in preparing the compound of Formula (II-a) or Formula (II-b). In some embodiments, the first base is a Grignard reagent such as an alkylmagnesium halide optionally complexed with a lithium halide, for example, iPrMgCl or iPrMgCl-LiCl; an alkyllithium reagent; an aryllithium reagent; or an inorganic hydride, such as sodium hydride or potassium hydride. In some embodiments, the first base is $R^1MgX^1$ or $R^1Li$; $R^1$ is methyl, ethyl, n-propyl, isopropyl, n-butyl, tert-butyl, or phenyl; and $X^1$ is Cl, Br, or I.

In some embodiments, the first base is $R^1MgX^1$ or $R^1Li$; $R^1$ is methyl, ethyl, n-propyl, isopropyl, n-butyl, tert-butyl, or phenyl; and $X^1$ is Cl, Br, or I, with the proviso that when $R^1$ is methyl, then $X^1$ is Cl or I. In some embodiments, the first base is $R^1MgX^1$ or $R^1Li$; $R^1$ is ethyl, n-propyl, isopropyl, n-butyl, tert-butyl, or phenyl; and $X^1$ is Cl, Br, or I. In some embodiments, the first base is $R^1MgX^1$ or $R^1Li$; $R^1$ is methyl, ethyl, n-propyl, isopropyl, n-butyl, tert-butyl, or phenyl; and $X^1$ is Cl or I. In some embodiments, the first base is $R^1MgX^1$ or $R^1Li$; $R^1$ is ethyl, n-propyl, isopropyl, n-butyl, tert-butyl, or phenyl; and $X^1$ is Cl or I.

In some embodiments, the first base is $R^1MgX^1$; $R^1$ is methyl, ethyl, n-propyl, isopropyl, n-butyl, tert-butyl, or phenyl; and $X^1$ is Cl, Br, or I, with the proviso that when $R^1$ is methyl, then $X^1$ is Cl or I. In some embodiments, the first base is $R^1MgX^1$; $R^1$ is ethyl, n-propyl, isopropyl, n-butyl, tert-butyl, or phenyl; and $X^1$ is Cl, Br, or I. In some embodiments, the first base is $R^1MgX^1$; $R^1$ is methyl, ethyl, n-propyl, isopropyl, n-butyl, tert-butyl, or phenyl; and $X^1$ is Cl or I. In some embodiments, the first base is $R^1MgX^1$; $R^1$ is ethyl, n-propyl, isopropyl, n-butyl, tert-butyl, or phenyl; and $X^1$ is Cl or I.

In some embodiments, the first base is $R^1MgX^1$. In some embodiments, $R^1$ is isopropyl or phenyl. In some embodiments, $R^1$ is isopropyl. In some embodiments, $R^1$ is phenyl. In some embodiments, $X^1$ is Cl. In some embodiments, the first base is iPrMgCl or PhMgCl. In some embodiments, the first base is iPrMgCl. In some embodiments, the first base is PhMgCl.

Any suitable metalating agent capable of effecting transmetallation of the compound of Formula (IV) can be used in preparing the compound of Formula (II-a) or Formula (II-b). For example, the metalating agent is a Grignard reagent such as an alkylmagnesium halide optionally complexed with a lithium halide, for example, iPrMgCl or iPrMgCl-LiCl; an alkyllithium reagent; or an aryllithium reagent. In some embodiments, the metalating agent is $R^2MgX^2$ or $R^2Li$; $R^2$ is methyl, ethyl, n-propyl, isopropyl, n-butyl, tert-butyl, or phenyl; and $X^2$ is Cl, Br, or I. In some embodiments, the metalating agent is $R^2MgX^2$. In some embodiments, $R^2$ is isopropyl or phenyl. In some embodiments, $R^2$ is isopropyl. In some embodiments, $R^2$ is phenyl. In some embodiments, $X^2$ is Cl. In some embodiments, the metalating agent is iPrMgCl or PhMgCl. In some embodiments, the metalating agent is iPrMgCl. In some embodiments, the metalating agent is PhMgCl.

In some embodiments, the first base and metalating agent are each alkyllithium reagents. In some embodiments, one of the first base and metalating agent is an alkyllithium reagent, and the other is a Grignard reagent. In some embodiments, the first base and metalating agent are each Grignard reagents. In some embodiments, the first base is PhMgCl; and the metalating agent is iPrMgCl. In some embodiments, the first base is PhMgCl; and the metalating agent is iPrMgCl-LiCl. In some embodiments, the first base is iPrMgCl; and the metalating agent is PhMgCl. In some embodiments, the first base is iPrMgCl; and the metalating agent is iPrMgCl. In some embodiments, the first base is iPrMgCl-LiCl; and the metalating agent is iPrMgCl-LiCl.

In some embodiments, the first base is PhMgCl; the metalating agent is iPrMgCl; and $M^a$ is MgCl. In some embodiments, the first base is PhMgCl; the metalating agent is iPrMgCl-LiCl; and $M^a$ is MgCl. In some embodiments, the first base is iPrMgCl; the metalating agent is PhMgCl; and $M^a$ is MgCl. In some embodiments, the first base is iPrMgCl; the metalating agent is iPrMgCl; and $M^a$ is MgCl. In some embodiments, the first base is iPrMgCl-LiCl; the metalating agent is iPrMgCl-LiCl; and $M^a$ is MgCl.

In some embodiments, the amine protecting agent is trimethylsilyl chloride (TMSCl); the first base is PhMgCl; the metalating agent is iPrMgCl; and $M^a$ is MgCl. In some embodiments, the amine protecting agent is triethylsilyl chloride (TESCl); the first base is PhMgCl; the metalating agent is iPrMgCl; and $M^a$ is MgCl. In some embodiments, the amine protecting agent is triisopropylsilyl chloride, tert-butyldimethylsilyl chloride (TBDMSCl), tert-butyldiphenylsilyl chloride (TBDPSCl), triphenylsilyl chloride, or 1,2-bis (chlorodimethylsilyl)ethane; the first base is PhMgCl; the metalating agent is iPrMgCl; and $M^a$ is MgCl.

In some embodiments, the first input mixture further comprises a first solvent. In some embodiments, the first output mixture further comprises a first solvent. In some embodiments, a first solvent is added to the first reactor. In some embodiments, a first solvent is added to the second reactor. Any suitable solvent can be used as the first solvent in preparing the compound of Formula (II-a) or Formula (II-b). Suitable solvents include, but are not limited to, ether solvents, such as tetrahydrofuran, 2-methyltetrahydrofuran, methyl tert-butyl ether, and cyclopentyl methyl ether; hydrocarbon solvents, such as toluene and n-heptane; and halogenated solvents, such as 1,2-dichloroethane, chloroform, and chlorobenzene. In some embodiments, the first input mixture further comprises a first solvent that is tetrahydrofuran (THF), 2-methyltetrahydrofuran, methyl tert-butyl ether, cyclopentyl methyl ether, toluene, n-heptane, 1,2-dichloroethane, chloroform, or chlorobenzene, or a combination thereof. In some embodiments, the first solvent is tetrahydrofuran (THF).

Any suitable reactor or combination of reactors known in the art can be used to prepare the compound of Formula (II-a) or Formula (II-b). Exemplary reactors that can be used to prepare the compound of Formula (II-a) or Formula (II-b) include, but are not limited to, batch reactors, continuous flow reactors, plug flow reactors, continuous tubular reactors, continuous stirred tank reactors, mixed flow reactors, semi-batch reactors, or combinations thereof. In some embodiments, one reactor is used. In some embodiments, two reactors are used. In some embodiments, three reactors are used.

In some embodiments, the first reactor and the second are different reactors. In some embodiments, the first reactor and the second reactor are the same type of reactor. In some embodiments, the first reactor and the second reactor are different types of reactors. In some embodiments, the first reactor and the second reactor are a single reactor. In some embodiments, the single reactor is a continuous flow reactor, a plug flow reactor, a continuous tubular reactor, or a mixed flow reactor. In some embodiments, the first reactor is a first reaction zone in the single reactor and the second reactor is a second reaction zone in the single reactor.

In some embodiments, one reactor having a first reaction zone and a second reaction zone is used to prepare a compound of Formula (II-a) or Formula (II-b). The first input mixture can be prepared in the first reaction zone of the reactor at a first set of reaction conditions, which includes a first temperature and a first pressure, for a first amount of time. The first input mixture can react to provide a first output mixture as the mixture moves from the first reaction zone to the second reaction zone. The compound of Formula (V) can be added into the second reaction zone of the reactor at a second set of reaction conditions, which includes a second temperature and a second pressure, for a second amount of time. In some embodiments, the one reactor having a first reaction zone and a second reaction zone is a plug flow reactor. In some embodiments, the one reactor having a first reaction zone and a second reaction zone is a continuous tubular reactor. In some embodiments, the one reactor having a first reaction zone and a second reaction zone comprises a recycle loop. In some embodiments, the first input mixture and the compound of Formula (V) are added separately. In some embodiments, the first input mixture is added to the first reaction zone and the compound of Formula (V) is added to the second reaction zone. In some embodiments, the first input mixture and the compound of Formula (V) are added simultaneously to the first reaction zone.

In some embodiments, one reactor having one reaction zone is used to prepare a compound of Formula (II-a) or Formula (II-b). The first input mixture and the compound of Formula (V) can be added into the one reaction zone at a first set of reaction conditions, which includes a first temperature and a first pressure, for a first amount of time. Then, the one reaction zone of the one reactor can be transitioned to a second set of reaction conditions, which includes a second temperature and a second pressure, for a second amount of time. In some embodiments, the one reactor having one reaction zone is a batch reactor. In some embodiments, the first input mixture is added to the one reaction zone at a first set of reaction conditions, then the compound of Formula (V) is added to the one reaction zone, and the one reactor is transitioned to a second set of reaction conditions. In some embodiments, the one reactor having one reaction zone is a semi-batch reactor. In some embodiments, the first input mixture and the compound of Formula (V) are added to the one reaction zone at a temperature from about −20 ° C. to about 20 ° C., at a pressure from about 0.1 bar to about 10 bar, for an amount of time from about 1 hour to about 24 hours to produce a compound of Formula (II-a) or Formula (II-b).

In some embodiments, two reactors including a first reactor and a second reactor are used to prepare a compound of Formula (II-a) or Formula (II-b). The first reactor can operate at a first set of reaction conditions including a first temperature and a first pressure. The second reactor can operate at a second set of reaction conditions including a second temperature and a second pressure. In some embodiments, the first reactor and the second reactor are the same type of reactor. In some embodiments, the first reactor and/or second reactor are batch reactors. In some embodiments, the first reactor and/or the second reactor are different types of reactor. In some embodiments, the first reactor and/or second reactor are semi-batch reactors. In some embodiments, the first reactor and second reactor are continuous stirred tank reactors.

Any suitable temperature can be used in the first reactor for preparing the compound of Formula (II-a) or Formula (II-b). The first reactor is maintained at a suitable first temperature to provide the first output mixture in an appropriate time and yield. In some embodiments, the first reactor is maintained at a first temperature of from about −78 ° C. to about 20 ° C. In some embodiments, the first reactor is cooled to a first temperature of from about −20 ° C. to about 0 ° C. In some embodiments, the first reactor is cooled to a first temperature of from about −20 ° C. to about −5 ° C. In some embodiments, the first reactor is cooled to a first temperature of from about −20 ° C. to about −10 ° C. In some embodiments, the first reactor is cooled to a first temperature of about −20 ° C.

The method of preparing the compound of Formula (II-a) or Formula (II-b) can be performed at any suitable pressure. For example, the first reactor can have a first pressure. A suitable first pressure can be less than atmospheric pressure, atmospheric pressure, or greater than atmospheric pressure. Other suitable first pressures can be, but are not limited to, 0.1 to 10 bar, 0.2 to 9 bar, 0.3 to 8 bar, 0.4 to 7 bar, 0.5 to 6 bar, 0.6 to 5 bar, 0.7 to 4 bar, 0.8 to 3 bar, 0.9 to 2 bar, or about 1 bar. In some embodiments, the first pressure can be atmospheric pressure. In some embodiments, the first pressure can be about 1 bar.

The method of preparing the compound of Formula (II-a) or Formula (II-b) can be performed for any suitable period of time. For example, a first period of time for preparing the compound of Formula (II-a) or Formula (II-b) can be, but is not limited to, 1 to 600 minutes, 30 to 600 minutes, 60 to 600 minutes, 60 to 300 minutes, 60 to 240 minutes, 60 to 180 minutes, 90 to 150 minutes, or about 120 minutes. In some embodiments, a first period of time for preparing the compound of Formula (II-a) or Formula (II-b) can be about 120 minutes. In some embodiments, a first period of time for preparing the compound of Formula (II-a) or Formula (II-b) can be about 90 minutes.

In some embodiments, the second input mixture further comprises a second solvent. In some embodiments, the second output mixture further comprises a second solvent. In some embodiments, a second solvent is added to the second reactor. In some embodiments, the second solvent is the same as the first solvent. In some embodiments, the second solvent is different from the first solvent. Any suitable solvent can be used as the second solvent in preparing the compound of Formula (II-a) or Formula (II-b). Suitable solvents include, but are not limited to, ether solvents, such as tetrahydrofuran, 2-methyltetrahydrofuran, methyl tent-butyl ether, and cyclopentyl methyl ether; hydrocarbon solvents, such as toluene and n-heptane; and halogenated solvents, such as 1,2-dichloroethane, chloroform, and chlorobenzene. In some embodiments, the second input mixture further comprises a second solvent that is tetrahydrofuran (THF), 2-methyltetrahydrofuran, methyl tert-butyl ether, cyclopentyl methyl ether, toluene, n-heptane, 1,2-dichloroethane, chloroform, or chlorobenzene, or a combination thereof. In some embodiments, the second solvent is tetrahydrofuran (THF).

Any suitable temperature can be used in the second reactor for preparing the compound of Formula (II-a) or Formula (II-b). The second reactor is maintained at a suitable temperature to provide the second output mixture comprising the compound of Formula (II-a) or Formula (II-b) in an appropriate time and yield. In some embodiments, the second reactor is maintained at a temperature of from about −20 ° C. to about 40 ° C. In some embodiments, the second reactor is maintained at a temperature of from about 10 ° C. to about 30 ° C. In some embodiments, the second reactor is maintained at a temperature of about 20 ° C.

The method of preparing the compound of Formula (II-a) or Formula (II-b) can be performed at any suitable pressure. For example, the second reactor can have a second pressure. A suitable second pressure can be less than atmospheric pressure, atmospheric pressure, or greater than atmospheric pressure. Other suitable first pressures can be, but are not limited to, 0.1 to 10 bar, 0.2 to 9 bar, 0.3 to 8 bar, 0.4 to 7 bar, 0.5 to 6 bar, 0.6 to 5 bar, 0.7 to 4 bar, 0.8 to 3 bar, 0.9 to 2 bar, or about 1 bar. In some embodiments, the first pressure can be atmospheric pressure. In some embodiments, the first pressure can be about 1 bar.

The method of preparing the compound of Formula (II-a) or Formula (II-b) can be performed for any suitable period of time. For example, a second period of time for preparing the compound of Formula (II-a) or Formula (II-b) can be, but is not limited to, 1 to 50 hours, 1 to 48 hours, 1 to 40 hours, 1 to 30 hours, 1 to 24 hours, 2 to 12 hours, 4 to 12 hours, 6 to 10 hours, 6 to 24 hours, 10 to 20 hours, or 12 to 18 hours. In some embodiments, a second period of time for preparing the compound of Formula (II-a) or Formula (II-b) can be about 8 hours. In some embodiments, a second period of time for preparing the compound of Formula (II-a) or Formula (II-b) can be from 12 to 18 hours.

The compound of Formula (II-a) or Formula (II-b) can be isolated by any suitable method known in the art, including concentration, extraction, trituration, crystallization, and/or chromatography.

In some embodiments, the method further comprises combining the second output mixture and an acid. In some embodiments, the acid comprises a Bronsted acid. In some embodiments, the acid comprises an organic acid or a mineral acid, or combinations thereof. In some embodiments, the acid comprises formic acid, acetic acid, citric acid, propanoic acid, butyric acid, benzoic acid, phosphoric acid, hydrochloric acid, trifluoroacetic acid, sulfuric acid, or combinations thereof In some embodiments, the acid comprises an organic acid. In some embodiments, the acid comprises formic acid, acetic acid, citric acid, propanoic acid, butyric acid, or benzoic acid. In some embodiments, the acid comprises acetic acid.

In some embodiments, the method of preparing a compound of Formula (II-a) or Formula (II-b) further comprises preparing the compound of Formula (V), the method comprising: (a1) forming a third reaction mixture comprising a compound of Formula (III):

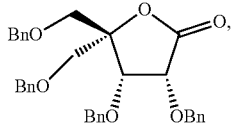

(III)

an amine of the formula H-R$^a$; and a third base that is R$^3$MgX$^3$ or R$^3$Li; wherein R$^3$ is methyl, ethyl, n-propyl, isopropyl, n-butyl, tent-butyl, or phenyl; and X$^3$ is Cl, Br, or I; thereby providing the compound of Formula (V).

In some embodiments, the amine has the formula

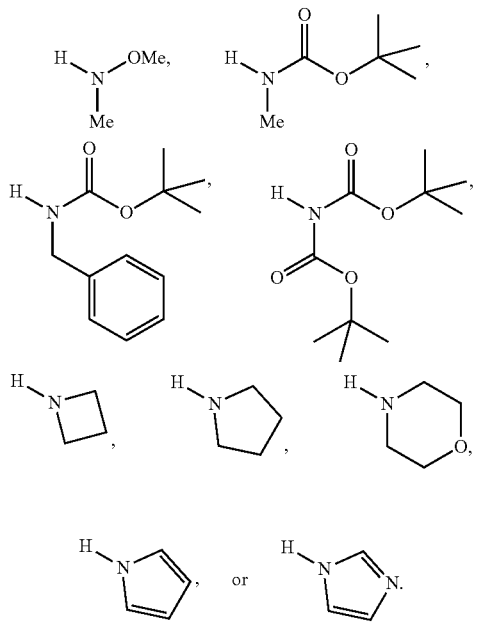

In some embodiments, the amine has the formula

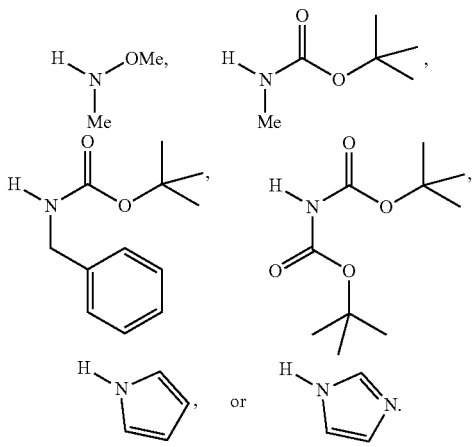

In some embodiments, the amine has the formula

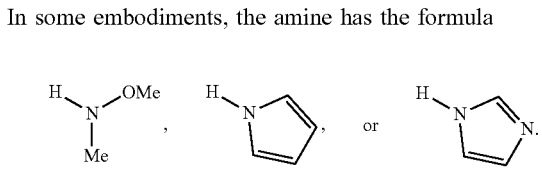

In some embodiments, the amine has the formula

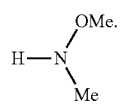

In some embodiments, X$^3$ is Cl, Br, or I. In some embodiments, X$^3$ is Br or I. In some embodiments, X$^3$ is Cl. In some embodiments, X$^3$ is Br. In some embodiments, X$^3$ is I.

In some embodiments, the third base is R$^3$MgX$^3$, wherein R$^3$ is methyl, ethyl, n-propyl, isopropyl, n-butyl, tent-butyl, or phenyl; and X$^3$ is Cl, Br, or I. In some embodiments, the third base is R$^3$MgX$^3$, wherein R$^3$ is methyl, isopropyl, n-butyl, tent-butyl, or phenyl; and X$^3$ is Cl or Br. In some embodiments, the third base is R$^3$MgCl, wherein R$^3$ is methyl, isopropyl, tent-butyl, or phenyl. In some embodiments, the third base is MeMgCl, iPrMgCl, or t-BuMgCl. In some embodiments, the third base is iPrMgCl.

In some embodiments, the amine has the formula

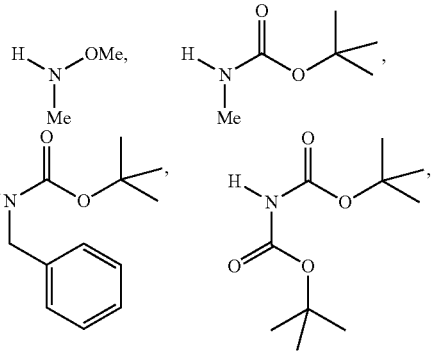

-continued

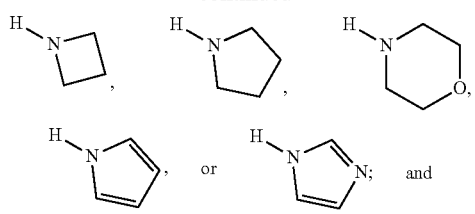

the third base is iPrMgCl.

In some embodiments, the amine has the formula

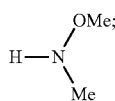

and the third base is iPrMgCl.

Any suitable solvent can be used in preparing the compound of Formula (V) in the method described herein. In some embodiments, the third reaction mixture further comprises a third solvent that is an ether solvent or a chlorinated solvent. In some embodiments, the third reaction mixture further comprises a third solvent that is tetrahydrofuran (THF), 2-methyltetrahydrofuran, methyl tert-butyl ether, cyclopentyl methyl ether, toluene, n-heptane, 1,2-dichloroethane, chloroform, or chlorobenzene, or a combination thereof. In some embodiments, the third reaction mixture further comprises a third solvent that is tetrahydrofuran (THF), 2-methyltetrahydrofuran, methyl tert-butyl ether, or a combination thereof In some embodiments, the third solvent is tetrahydrofuran (THF).

Any suitable temperature can be used in preparing the compound of Formula (V). In some embodiments, the third reaction mixture is maintained at a temperature of from about −78 ° C. to about 40 ° C. In some embodiments, the third reaction mixture is maintained at a temperature of from about −20 ° C. to about 25 ° C. In some embodiments, the third reaction mixture is maintained at a temperature of from about 0 ° C. to about 25 ° C. In some embodiments, the third reaction mixture is maintained at a temperature of from about 10 ° C. to about 25 ° C. In some embodiments, the third reaction mixture is maintained at a temperature of from about 15 ° C. to about 25 ° C. In some embodiments, the third reaction mixture is maintained at a temperature of about 20 ° C.

In some embodiments, the compound of Formula (II-a) or Formula (II-b) has the structure:

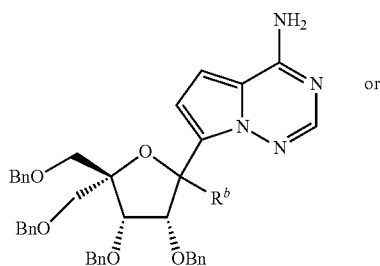

-continued

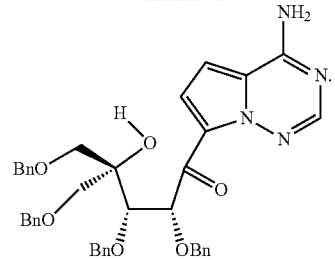

In some embodiments, the method comprises: (a1) forming a third reaction mixture comprising the compound of Formula (III) having the structure:

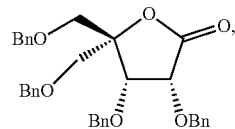

the amine having the formula

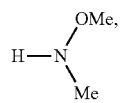

and iPrMgCl, thereby forming the compound of Formula (V) having the structure:

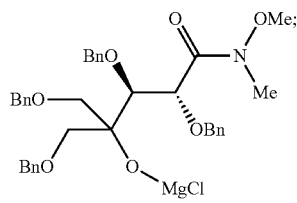

(a) preparing the first input mixture in the first reactor, wherein the first input mixture comprises TMS-Cl, PhMgCl, iPrMgCl, and the compound of Formula (IV) having the structure:

wherein the first reactor provides the first output mixture; and (b) adding the first output mixture and the compound of Formula (V) to the second reactor thereby forming the compound of Formula (II-a) or Formula (II-b) having the structure:

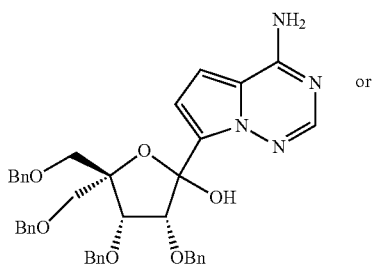 or 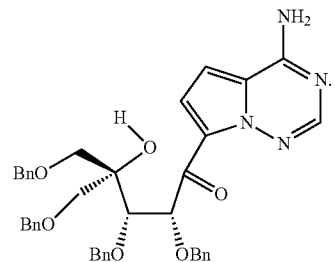

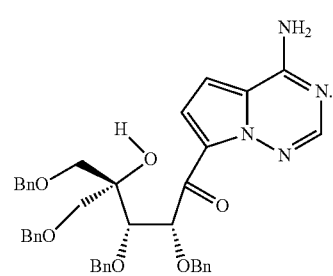

The compound of Formula (II-a) having the structure:

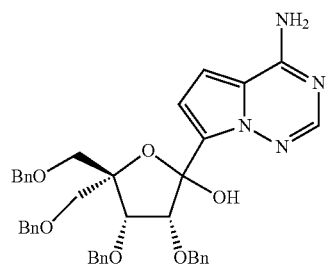

is also known as (3R,4S)-2-(4-aminopyrrolo[2,1-f][1,2,4]triazin-7-yl)-3,4-bis(benzyloxy)-5,5-bis((benzyloxy)methyl)tetrahydrofuran-2-ol.

As is generally understood in the art, the compound of Formula (II-a) having the structure:

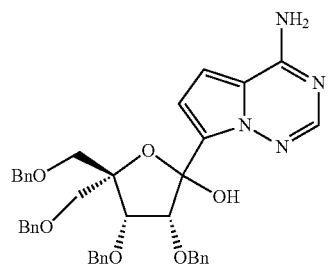

exists in an equilibrium with a compound of Formula (II-b) having the structure:

Accordingly, as used herein, the compound of Formula (II-a) having the above structure when recited alone is understood to mean the compound of Formula (II-a) and/or the compound of Formula (II-b) or any combination of the two species.

The method of the present disclosure is amenable to synthesis of gram to kilogram quantities of the compound of Formula (II-a) or Formula (II-b) from the compound of Formula (III). In some embodiments, the third reaction mixture comprises at least 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 500 kg, or at least 1000 kg or more of the compound of Formula (III). In some embodiments, the third reaction mixture comprises at least 1 kg of the compound of Formula (III). In some embodiments, the third reaction mixture comprises from about 50 g to about 100 kg, e.g., from about 50 g to about 20 kg, or from about 30 g to about 20 kg, of the compound of Formula (III). In some embodiments, the third reaction mixture comprises from about 5 kg to about 15 kg of the compound of Formula (III). For example, in some embodiments, the third reaction mixture comprises about 10 kg of the compound of Formula (III).

The compound of Formula (IV) having the structure:

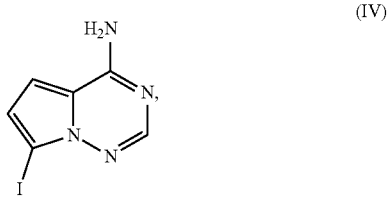

is also known as 7-iodopyrrolo[2,1-f][1,2,4]triazin-4-amine.

The methods of the present disclosure can provide the compound of Formula (II-a) or Formula (II-b) from the compound of Formula (III) or the compound of Formula (V) in any suitable yield. For example, the compound of Formula (II-a) or Formula (II-b) can be prepared in a yield of at least 50%, 55%, 60%, 65%, 70%, 75%, 80%, 85%, 90%, 95%, 97%, 98%, or at least 99%. In some embodiments, the yield of Formula (II-a) or Formula (II-b) is from about 60% to about 100%. In some embodiments, the yield of Formula (II-a) or Formula (II-b) is from about 70% to about 80% or from about 75% to about 85%. In some embodiments, the yield of Formula (II-a) or Formula (II-b) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of Formula (II-a) or Formula (II-b) is about 79%. In some embodiments, the yield of Formula (II-a) or Formula (II-b)

is from about 60% to about 90%. In some embodiments, the yield of Formula (II-a) or Formula (II-b) is from about 70% to about 90%. In some embodiments, the yield of Formula (II-a) or Formula (II-b) is from about 70% to about 80%. In some embodiments, the yield of Formula (II-a) or Formula (II-b) is from about 75% to about 85%.

The methods of the present disclosure can provide the compound of Formula (II-a) or Formula (II-b) from the compound of Formula (III) or the compound of Formula (V) in any suitable purity. For example, the compound of Formula (II-a) or Formula (II-b) can be prepared in a purity of from about 90% to about 100%, such as from about 95% to about 100% or from about 98% to about 100%. In some embodiments, the purity of the compound of Formula (II-a) or Formula (II-b) is from about 98% to about 100%. In some embodiments, the compound of Formula (II-a) or Formula (II-b) is prepared in a purity of about 90%, about 95%, about 96%, about 97%, about 98%, about 99%, about 99.9%, about 99.99%, about 99.999%, about 99.9999%, or about 99.99999%. In some embodiments, the compound of Formula (II-a) or Formula (II-b) is prepared in a purity of about 99.92%. In some embodiments, the compound of Formula (II-a) or Formula (II-b) is prepared in a purity of from about 95% to about 99.999%, from about 98% to about 99.999%, from about 98% to about 99.99%, or from about 99% to about 99.99%. In some embodiments, the purity of the compound of Formula (II-a) or Formula (II-b) is from about 90% to about 100%.

In some embodiments, the method further comprises: (c) forming a fourth reaction mixture comprising a Lewis acid or Bronsted acid, a reducing agent, and the compound of Formula (II-a) or Formula (II-b) having the structure:

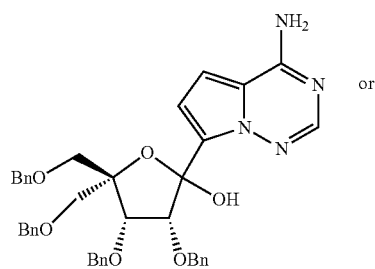

or

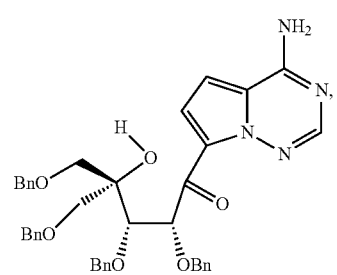

thereby forming the compound of Formula (II-a) having the structure:

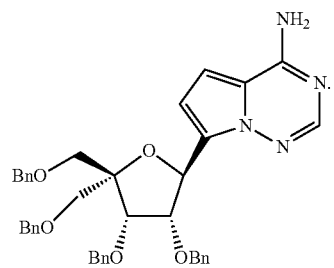

In some embodiments, the method comprises:
(a1) forming the third reaction mixture comprising the compound of Formula (III) having the structure:

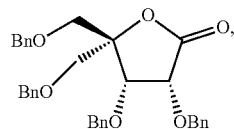

the amine having the formula

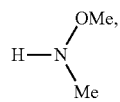

and iPrMgCl, thereby forming the compound of Formula (V) having the structure:

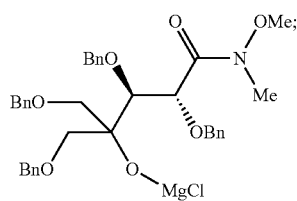

(a) preparing the first input mixture in the first reactor, wherein the first input mixture comprises TMS-Cl, PhMgCl, iPrMgCl, and the compound of Formula (IV) having the structure:

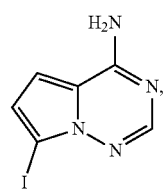

wherein the first reactor provides the first output mixture;

(b) adding the first output mixture and the compound of Formula (V) to the second reactor thereby forming the compound of Formula (II-a) or Formula (II-b) having the structure:

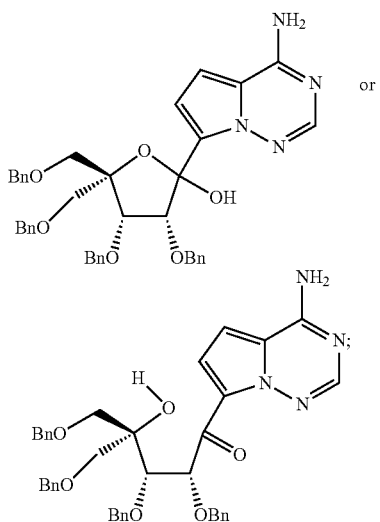

and (c) forming the fourth reaction mixture comprising the Lewis acid or Bronsted acid, the reducing agent, and the compound of Formula (II-a) or Formula (II-b) having the structure:

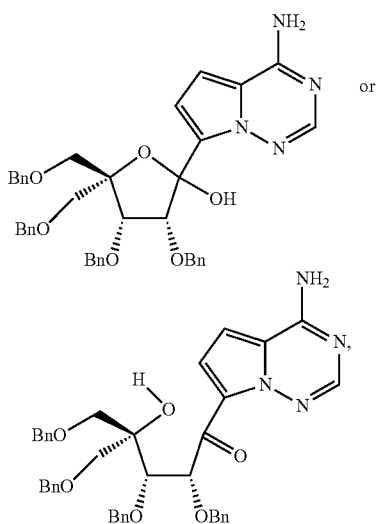

thereby forming the compound of Formula (II-a) having the structure:

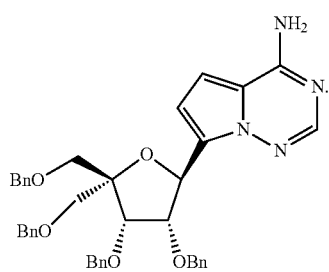

In some embodiments, the Lewis acid or Bronsted acid comprises boron trifluoride diethyl etherate (BF$_3$·Et$_2$O), formic acid, acetic acid, dichloroacetic acid, trifluoroacetic acid, trimethylsilyl triflate, TiCl$_4$, SnCl$_4$, or FeCl$_3$. In some embodiments, the Lewis acid or Bronsted acid comprises boron trifluoride diethyl etherate (BF$_3$·Et$_2$O).

Any suitable reducing agent known in the art can be used in the fourth reaction mixture for preparing the compound of Formula (II-a). Suitable reducing agents include, but are not limited to, trialkylsilanes, arylsilanes such as triarylsilanes, borohydrides, aluminum hydrides, trialkyltin hydrides, and triaryltin hydrides. In some embodiments, the reducing agent comprises triethylsilane, tert-butyldimethylsilane, phenylsilane, triphenylsilane, trimethylsilane, sodium borohydride, sodium cyanoborohydride, sodium triacetoxyborohydride, lithium aluminum hydride, or tri-n-butyltin hydride. In some embodiments, the reducing agent comprises triethylsilane.

Other suitable reducing agents include catalysts in combination with a hydride source, such as hydrogen gas. In some embodiments, the method further comprises a catalyst. In some embodiments, the method further comprises a transition metal catalyst. Suitable transition metal catalysts include palladium catalysts, such as palladium hydroxide, palladium on carbon, and Pd(X$^5$)$_2$ (X$^5$=Cl, Br, I, or carboxylate such as formate or acetate), and platinum catalysts, such as platinum hydroxide, platinum on carbon, and Pd(X$^5$)$_2$ (X$^5$=Cl, Br, I, or carboxylate such as formate or acetate).

Any suitable solvent can be used for the fourth reaction mixture to prepare the compound of Formula (II-a). Suitable solvents include ether solvents, such as tetrahydrofuran, 2-methyltetrahydrofuran, methyl tert-butyl ether, or cyclopentyl methyl ether; hydrocarbon solvents, such as toluene or n-heptane; halogenated solvents, such as 1,2-dichloroethane, chloroform, or chlorobenzene; alcoholic solvents, such as methanol, ethanol, 2,2,2-trifluoroethanol, or isopropanol; ester solvents, such as ethyl acetate or isopropyl acetate; and acid solvents such as acetic acid. In some embodiments, the fourth reaction mixture further comprises a fourth solvent that is acetonitrile, tetrahydrofuran, 2-methyltetrahydrofuran, methyl tert-butyl ether, cyclopentyl methyl ether, toluene, n-heptane, methylene chloride, 1,2-dichloroethane, chloroform, chlorobenzene, methanol, ethanol, 2,2,2-trifluoroethanol, isopropanol, ethyl acetate, isopropyl acetate, acetic acid, or a combination thereof. In some embodiments, the fourth solvent is acetonitrile.

Any suitable temperature can be used for the fourth reaction mixture to prepare the compound of Formula (II-a). In some embodiments, the fourth reaction mixture is maintained at a temperature of from about −78 °C. to about 40 °C. In some embodiments, the fourth reaction mixture is maintained at a temperature of from about −25 °C. to about −15 °C.

In some embodiments, the method comprises: (c) forming the fourth reaction mixture comprising boron trifluoride diethyl etherate (BF$_3$·Et$_2$O), triethylsilane, acetonitrile, and the compound of Formula (II-a) or Formula (II-b) having the structure:

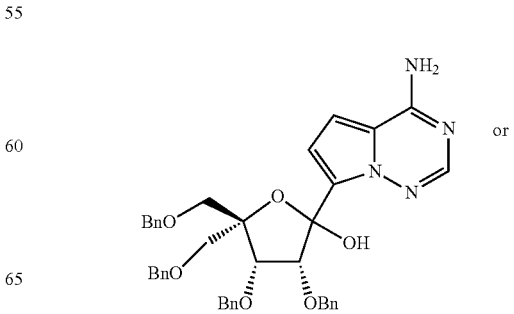

-continued

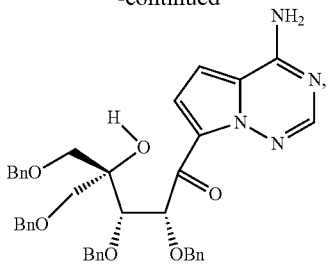

thereby forming the compound of Formula (II-a) having the structure:

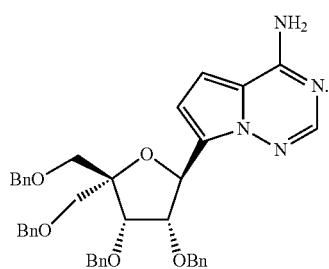

IV. EXAMPLES

Example 1. Synthesis of (3R,4S)-2-(4-aminopyrrolo[2,1-f][1,2,4]triazin-7-yl)-3,4-bis (benzyloxy)-5,5-bis((benzyloxy)methyl)tetrahydrofuran-2-ol A reactor was charged with 7-iodopyrrolo[2,1-f][1,2,4]triazin-4-amine (Formula (IV), 1.2 equiv) and tetrahydrofuran (4 volumes). The contents were cooled to about 0 °C. and trimethylsilyl chloride (2.4 equiv) was charged. After about 30 minutes of agitation, the contents were cooled to about −10 °C. and phenylmagnesium chloride (2.4 equiv) was added while maintaining the temperature below 0 °C. The contents were then agitated for about 30 min at about −10 °C. before adjusting to about −20 °C. Isopropylmagnesium chloride (1.2 equiv) was added while maintaining the temperature below −10 °C. The contents were adjusted to about −20 °C. and agitated for about 30 minutes. A second reactor was charged with (3R,4S)-3,4-bis (benzyloxy)-5,5-bis((benzyloxy)methyl)dihydrofuran-2(3H)-one (Formula (III), 1.0 equiv), N, O-dimethylhydroxylamine hydrochloride (1.1 equiv) and tetrahydrofuran (4 volumes). The contents were cooled to about −20 °C. and isopropylmagnesium chloride (2.3 equiv) was added while maintaining the temperature below −10 °C. The contents were adjusted to about −20 °C. and agitated for about 1 hour. The contents from the two reactors were combined while maintaining the temperature below −15 °C. and then rinsed forward with tetrahydrofuran (1 volume). The mixture was warmed to about 20 °C. over about 1 hour and then agitated for about 12-18 hours at 20 °C. A 20% aqueous acetic acid solution (4 volumes) was added followed by ethyl acetate (9 volumes) and the mixture was agitated at about 20 °C. for about 15 minutes. The layers were separated (aqueous discarded) and 5 wt% aqueous hydrochloric acid (4 volumes) was added. The mixture was agitated at about 20 °C. for about 15 minutes and then the layers were separated (aqueous discarded). Additional 5 wt% aqueous hydrochloric acid (4 volumes) was added and the mixture was agitated at about 20 °C. for about 15 minutes. The layers were separated (aqueous discarded) and additional 5 wt% aqueous hydrochloric acid (4 volumes) was added. The mixture was agitated at about 20 °C. for about 15 minutes and then the layers were separated (aqueous discarded). A 20 wt% aqueous potassium carbonate solution (4 volumes) was added and the mixture was agitated at about 20 °C. for about 15 minutes. The layers were separated (aqueous discarded) and a 5 wt% aqueous sodium chloride solution (4 volumes) was added. The mixture was agitated at about 20 °C. for about 15 minutes and then the layers were separated (aqueous discarded). The reactor contents were concentrated under vacuum to a minimum volume to provide crude (3R,4S)-2-(4-aminopyrrolo[2,1-f][1,2,4]triazin-7-yl)-3,4-bis (benzyloxy)-5,5-bis((benzyloxy)methyl)tetrahydrofuran-2-ol, a compound of Formula (II-a), that was used in the next step.

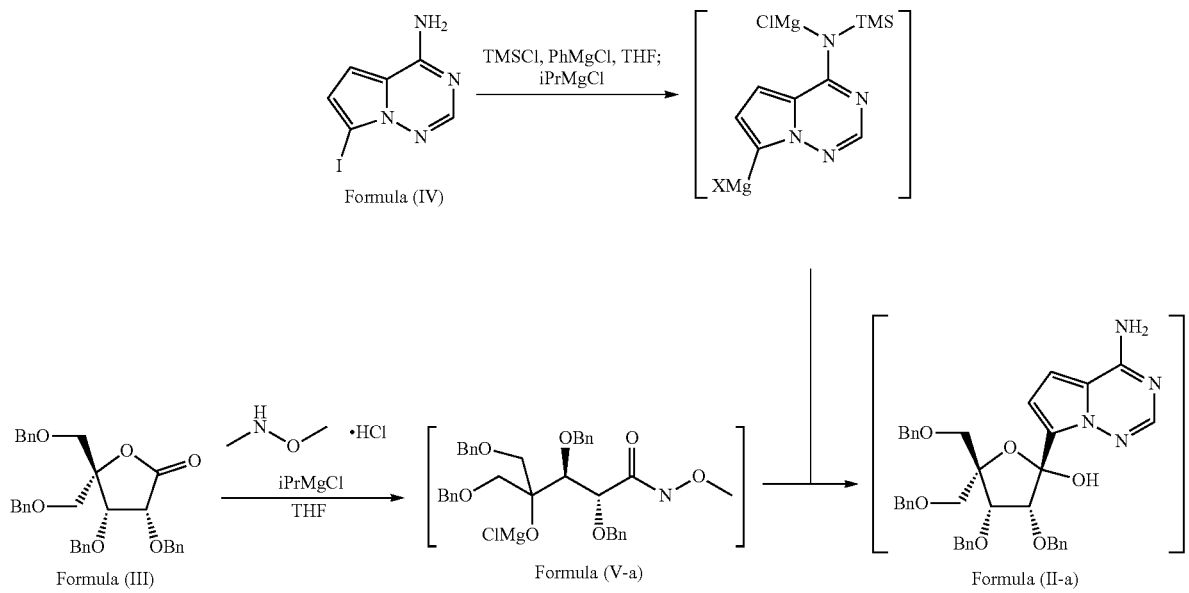

Example 2. Synthesis of 7-((2S,3S,4S)-3,4-bis(benzyloxy)-5,5-bis ((benzyloxy)methyl)tetrahydrofuran-2-yl)pyrrolo[2,1-f][1,2,4]triazin-4-amine

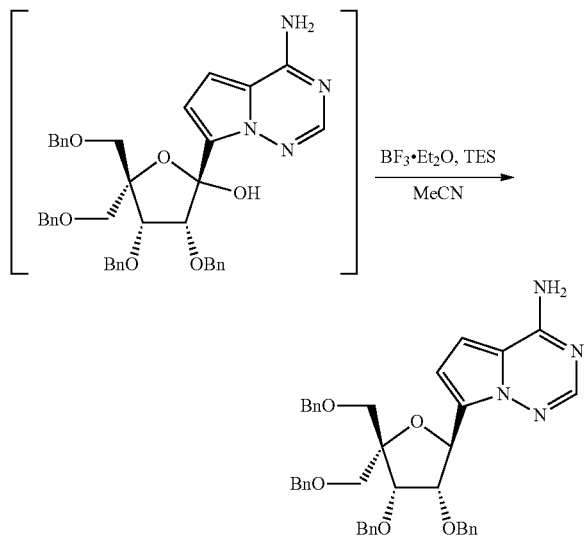

A reactor was charged with crude (3R,4S)-2-(4-aminopyrrolo[2,1-f][1,2,4]triazin-7-yl)-3,4-bis (benzyloxy)-5,5-bis ((benzyloxy)methyl)tetrahydrofuran-2-ol (1.0 equiv.) and acetonitrile (4 volumes.) The reactor contents were concentrated under vacuum to a minimum volume and then acetonitrile (4 volumes) was charged. The concentration under vacuum to a minimum volume was repeated and then acetonitrile (8 volumes) was charged. The contents were cooled to about −25 to −15 ° C. and triethylsilane (2.7 equiv.,) was charged. Boron trifluoride diethyl ether (2.0 equiv) was added while maintaining the temperature below −15 ° C. and the contents were then agitated for about 1 hour at about −20 ° C. The contents were adjusted to about 0 to 10 ° C. before an aqueous 5 wt% solution of sodium hydroxide (7 volumes) was added while maintaining the temperature below 20 ° C. The mixture was agitated for about 18 hours and then the layers were discharged into separate containers. The aqueous layer was returned to the reactor. Ethyl acetate (5 volumes) was added and the mixture was agitated for about 15 minutes. The aqueous layer was discharged from the reactor and the first organic layer was returned to the reactor. The combined organic layers were concentrated under vacuum to a minimum volume and then methanol (2 volumes) was charged. The contents were then concentrated under vacuum to a minimum volume and then methanol (2 volumes) was charged. The contents were again concentrated under vacuum to a minimum volume and then methanol (2 volumes) was charged. The contents were concentrated under vacuum to a minimum volume and ethyl acetate (9 volumes) was charged. A 5 wt% aqueous solution of sodium chloride (5 volumes) was added and the mixture was agitated for about 15 minutes. The aqueous layer was discharged and activated carbon (0.3 g/g) was charged. The contents were adjusted to about 30 ° C. to 40 ° C. and agitated for about 30 minutes. Agitation was stopped and the mixture was allowed to settle for about 15 minutes. The reactor contents were then filtered through Celite (1 g/g), rinsing forward with ethyl acetate (2 volumes). The filtrate was then returned to the reactor and activated carbon (0.3 g/g) was added. The contents were adjusted to about 30 ° C. to 40 ° C. and agitated for about 30 minutes. Agitation was stopped and the mixture was allowed to settle for approximately 15 minutes. The reactor contents were then filtered through Celite (1 g/g), rinsing forward with ethyl acetate (2 volumes). The filtrate was concentrated under vacuum to a minimum volume. The crude product was purified by chromatography using ethyl acetate and heptane to afford 7-((2S,3S,4S)-3,4-bis(benzyloxy)-5,5-bis((benzyloxy)methyl)tetrahydrofuran-2-yl) pyrrolo[2,1-f][1,2,4]triazin-4-amine. $^1$H NMR (400 MHz, CDCl$_3$)δ7.89 (s, 1H), 7.43-7.15 (m, 20H), 6.70 (d, J=4.5 Hz, 1H), 6.50 (d, J=4.5 Hz, 1H), 5.70 (d, J=5.8 Hz, 2H), 4.76-4.48 (m, 10H), 4.38 (d, J=5.2 Hz, 1H), 4.01 (d, J=10.4 Hz, 1H), 3.89 (d, J=10.4 Hz, 1H), 3.84 (s, 2H).

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a compound of Formula (II-a) or Formula (II-b):

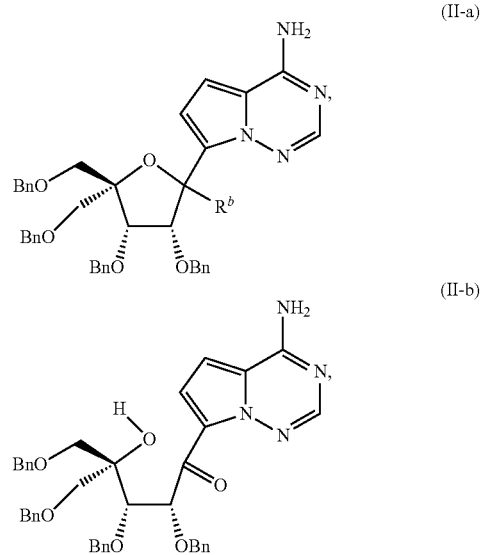

comprising:
(a) preparing a first input mixture, wherein the first input mixture comprises an amine protecting agent, a first base, a metalating agent, and a compound of Formula (IV):

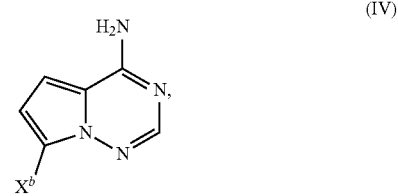

to provide a first output mixture; and (b) preparing a second input mixture comprising the first output mixture and a compound of Formula (V) to provide a second output mixture comprising the compound of Formula (II-a) or Formula (II-b), wherein the compound of Formula (V) has the structure:

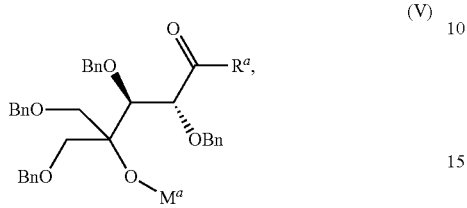

wherein
$R^a$ is

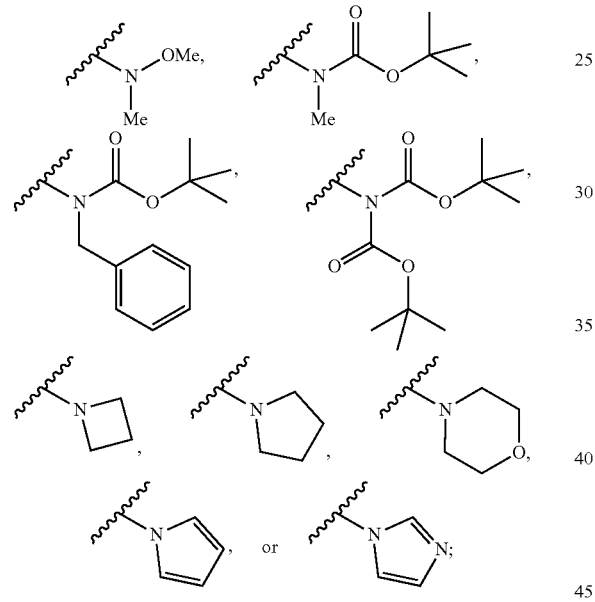

$M^a$ is Li or $MgX^a$;
$X^a$ is Cl, Br, or I;
$R^b$ is hydrogen or —OH; and
$X^b$ is Cl, Br, or I.

2. The method of claim 1, for preparing the compound of Formula (II-a) or Formula II b):

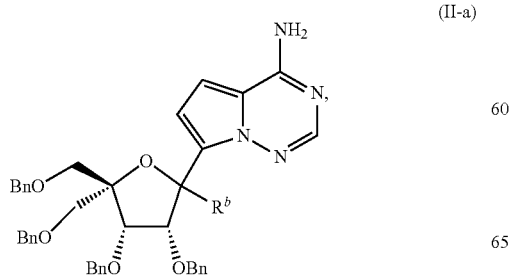

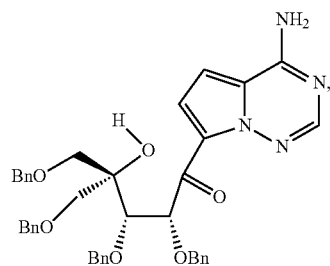

comprising:

(a) preparing the first input mixture in a first reactor, wherein the first input mixture comprises an amine protecting agent, the first base, the metalating agent, and the compound of Formula (IV):

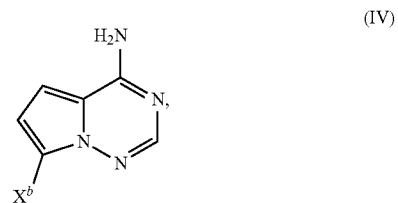

wherein the first reactor provides the first output mixture; and (b) adding the first output mixture and the compound of Formula (V) to form the second input mixture in a second reactor, wherein the compound of Formula (V) has the structure:

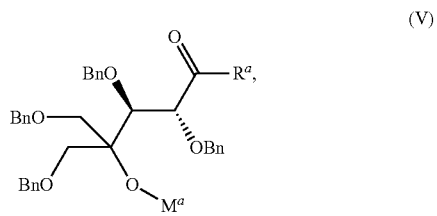

wherein
$R^a$ is

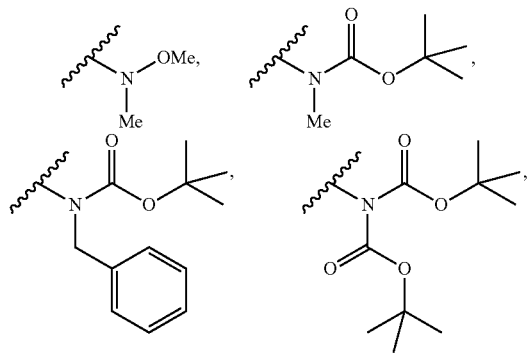

-continued

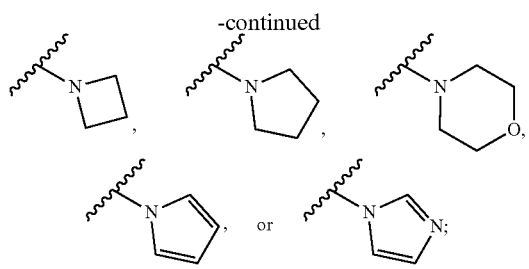

$M^a$ is Li or $MgX^a$;
$X^a$ is Cl, Br, or I;
$R^b$ is hydrogen or —OH;
$X^b$ is Cl, Br, or I; and
the second reactor provides the second output mixture comprising the compound of Formula (II-a) or Formula (II-b).

3. The method of claim 2, wherein the method comprises:
(a1) forming a third reaction mixture comprising the compound of Formula (III) having the structure:

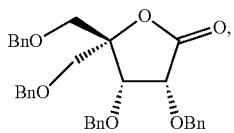

the amine having the formula

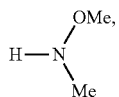

and iPrMgCl, thereby forming the compound of Formula (V) having the structure:

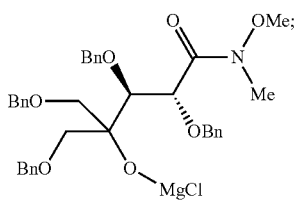

(a) adding the first input mixture to the first reactor, wherein the first input mixture comprises TMS-Cl, PhMgCl, iPrMgCl, and the compound of Formula (IV) having the structure:

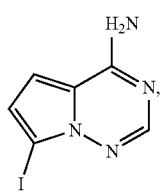

wherein the first reactor provides the first output mixture; and (b) adding the first output mixture and the compound of Formula (V) to the second reactor thereby forming the compound of Formula (II-a) or Formula (II-b) having the structure:

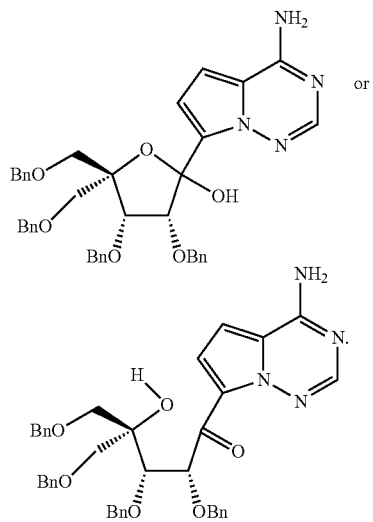

4. The method of claims 2, wherein the first reactor and the second are different reactors.

5. The method of claim 2, wherein the first reactor and the second reactor are the same type of reactor.

6. The method of claim 2, wherein the first reactor and the second reactor are different types of reactors.

7. The method of claims 2, wherein the first reactor and the second reactor are a single reactor.

8. The method of claim 7, wherein the single reactor is a continuous flow reactor, a plug flow reactor, a continuous tubular reactor, or a mixed flow reactor.

9. The method of claim 7, wherein the first reactor is a first reaction zone in the single reactor and the second reactor is a second reaction zone in the single reactor.

10. The method of claim 1, wherein the amine protecting agent is trifluoroacetic anhydride, di(tert-butyl) dicarbonate, trimethylsilyl chloride (TMSCl), triethylsilyl chloride (TESCl), triisopropylsilyl chloride, tert-butyldimethylsilyl chloride (TBDMSCl), tert-butyldiphenylsilyl chloride (TBDPSCl), triphenylsilyl chloride, or 1,2-bis (chlorodimethylsilyl)ethane.

11. The method of claim 1, wherein the first base is $R^1MgX^1$ or $R^1Li$;
$R^1$ is methyl, ethyl, n-propyl, isopropyl, n-butyl, tert-butyl, or phenyl; and
$X^1$ is Cl, Br, or I.

12. The method of claim 1, wherein the metalating agent is $R^2MgX^2$ or $R^2Li$;
$R^2$ is methyl, ethyl, n-propyl, isopropyl, n-butyl, tert-butyl, or phenyl; and
$X^2$ is Cl, Br, or I.

13. The method of claim 1, wherein the amine protecting agent is trimethylsilyl chloride (TMSCl);
the first base is PhMgCl;
the metalating agent is iPrMgCl; and
$M^a$ is MgCl.

14. The method of claim 1, wherein the first input mixture further comprises a first solvent that is tetrahydrofuran (THF), 2-methyltetrahydrofuran, methyl tert-butyl ether, cyclopentyl methyl ether, toluene, n-heptane, 1,2-dichloroethane, chloroform, or chlorobenzene, or a combination thereof.

15. The method of claim 1, wherein the second input mixture further comprises a second solvent that is tetrahydrofuran (THF), 2-methyltetrahydrofuran, methyl tert-butyl ether, cyclopentyl methyl ether, toluene, n-heptane, 1,2-dichloroethane, chloroform, or chlorobenzene, or a combination thereof.

16. The method of claim 1, further comprising combining the second output mixture and an acid.

17. The method of claim 16, wherein the acid comprises formic acid, acetic acid, citric acid, propanoic acid, butyric acid, or benzoic acid.

18. The method of claim 1, further comprising preparing the compound of Formula (V), the method comprising:

(a1) forming a third reaction mixture comprising a compound of Formula (III):

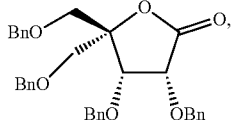

an amine of the formula H-R$^a$; and
a third base that is R$^3$MgX$^3$ or R$^3$Li; wherein
R$^3$ is methyl, ethyl, n-propyl, isopropyl, n-butyl, tert-butyl, or phenyl; and
X$^3$ is Cl, Br, or I;
thereby providing the compound of Formula (V).

19. The method of claim 18, wherein the amine has the formula

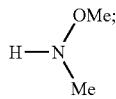

and the third base is iPrMgCl.

20. The method of claim 18, wherein the third reaction mixture further comprises a third solvent that is tetrahydrofuran (THF), 2-methyltetrahydrofuran, methyl tert-butyl ether, cyclopentyl methyl ether, toluene, n-heptane, 1,2-dichloroethane, chloroform, or chlorobenzene, or a combination thereof.

21. The method of claim 1, wherein the yield of the compound of Formula (II-a) or Formula (II-b) is from about 60% to about 90%.

22. The method of claim 1, wherein the purity of the compound of Formula (II-a) or Formula (II-b) is from about 90% to about 100%.

23. The method of claim 1, further comprising:

(c) forming a fourth reaction mixture comprising a Lewis acid or Bronsted acid, a reducing agent, and the compound of Formula (II-a) or Formula (II-b) having the structure:

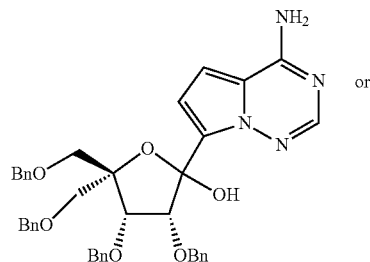

thereby forming the compound of Formula (II-a) having the structure:

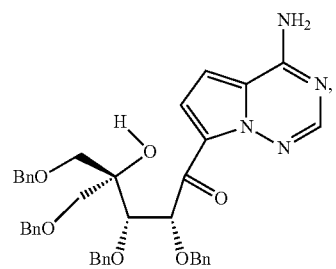

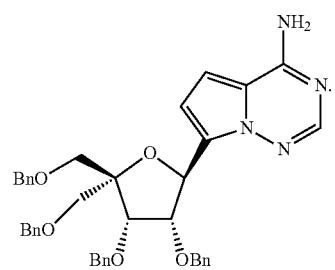

24. The method of claim 23, wherein the method comprises:

(a1) forming the third reaction mixture comprising the compound of Formula (III) having the structure:

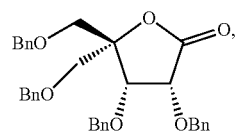

the amine having the formula

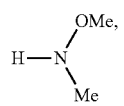

and iPrMgCl, thereby forming the compound of Formula (V) having the structure:

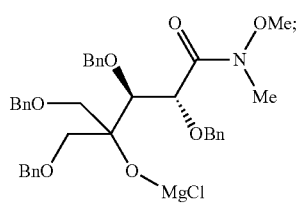

(a) adding the first input mixture to the first reactor, wherein the first input mixture comprises TMS-Cl, PhMgCl, iPrMgCl, and the compound of Formula (IV) having the structure:

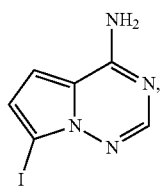 [SMILES: Nc1ncnn2c(I)ccc12]

wherein the first reactor provides the first output mixture;

(b) adding the first output mixture and the compound of Formula (V) to the second reactor thereby forming the compound of Formula (II-a) or Formula (II-b) having the structure:

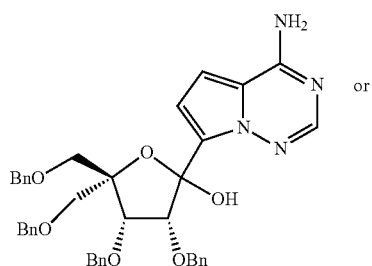

and (c) forming the fourth reaction mixture comprising the Lewis acid or Bronsted acid, the reducing agent, and the compound of Formula (II-a) or Formula (II-b) having the structure:

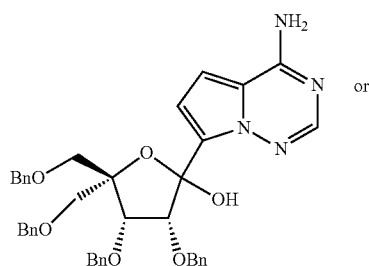

thereby forming the compound of Formula (II-a) having the structure:

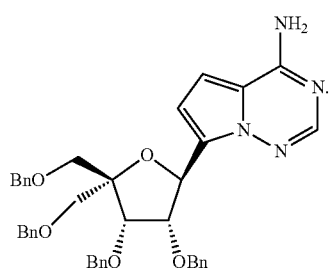

25. The method of claim 23, wherein the Lewis acid or Bronsted acid comprises boron trifluoride diethyl etherate ($BF_3 \cdot Et_2O$), formic acid, acetic acid, dichloroacetic acid, trifluoroacetic acid, trimethylsilyl triflate, $TiCl_4$, $SnCl_4$, or $FeCl_3$.

26. The method of claim 23, wherein the reducing agent comprises triethylsilane, tert-butyldimethylsilane, phenylsilane, triphenylsilane, trimethylsilane, sodium borohydride, sodium cyanoborohydride, sodium triacetoxyborohydride, lithium aluminum hydride, or tri-n-butyltin hydride.

27. The method of claim 23, wherein the fourth reaction mixture further comprises a fourth solvent that is acetonitrile, tetrahydrofuran, 2-methyltetrahydrofuran, methyl tert-butyl ether, cyclopentyl methyl ether, toluene, n-heptane, methylene chloride, 1,2-dichloroethane, chloroform, chlorobenzene, methanol, ethanol, 2,2,2-trifluoroethanol, isopropanol, ethyl acetate, isopropyl acetate, acetic acid, or a combination thereof.

28. The method of claim 23, wherein the method comprises:

(c) forming the fourth reaction mixture comprising boron trifluoride diethyl etherate ($BF_3 \cdot Et_2O$), triethylsilane, acetonitrile, and the compound of Formula (II-a) or Formula (II-b) having the structure:

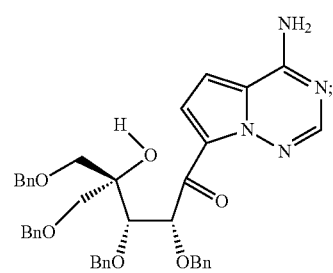

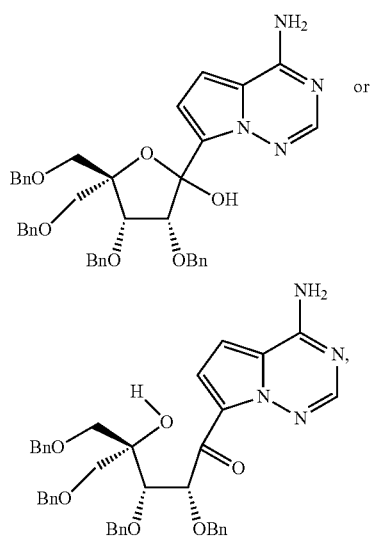
thereby forming the compound of Formula (II-a) having the structure:
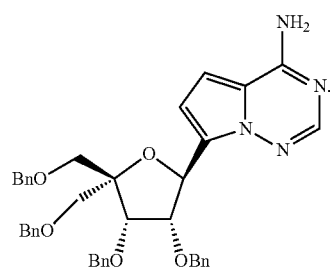
* * * * *